United States Patent
Mark et al.

(10) Patent No.: US 6,664,068 B2
(45) Date of Patent: Dec. 16, 2003

(54) PABLO, A POLYPEPTIDE THAT INTERACTS WITH BCL-XL, AND USES RELATED THERETO

(75) Inventors: Robert Mark, Lawrenceville, NJ (US); Kathleen H. Young, Newtown, PA (US); Andrew T. Wood, Newtown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/116,370

(22) Filed: Apr. 4, 2002

(65) Prior Publication Data

US 2003/0190709 A1 Oct. 9, 2003

Related U.S. Application Data

(62) Division of application No. 09/425,501, filed on Oct. 22, 1999.

(51) Int. Cl.$^7$ ................ G01N 33/53; C07K 17/00; C07K 16/00; A61K 39/395
(52) U.S. Cl. ................ 435/7.1; 530/350; 530/388.22; 530/387.7; 424/130.1; 424/134.1
(58) Field of Search ................ 530/350, 388.22, 530/387.7; 424/130.1, 134.1; 435/7.1

(56) References Cited

U.S. PATENT DOCUMENTS 5,656,725 A  8/1997  Chittenden et al.

FOREIGN PATENT DOCUMENTS

| WO | WO 93/16178 | 8/1993 |
| WO | WO 96/35951 | * 11/1996 |

OTHER PUBLICATIONS

Nagase et al. DNA Research, vol. 3, pp. 321–329, 1996.*
Kiefer et al. Nature, vol. 374, pp. 736–739, Apr. 1995.*
Bear, James E. et al. (1998) "SCAR, a WASP–related Protein, Isolated as a Suppressor of Receptor Defects in Late dictyostelium Development" *The Journal of Cell Biology* 142(5):1325–35.
Derry, Jonathan M. J. et al. (1994) "Isolation of a Novel Gene Mutated in Wiskott–Aldrich Syndrome" *Cell* 78:635–44.
Holinger, Eric P. (1999) "Bak BH3 Peptides Antagonize Bcl–$x_L$ Function and Induce Apoptosis through Cytochrome c–independent Activation of Caspases" *The Journal of Biological Chemistry* 274(19):13298–13304.
Korsmeyer, Stanley J. (1999) "BCL–2 Gene Family and the Regulation of Programmed Cell Death" *Cancer Research (Suppl.)* 59:1693s–1700s.
Machesky, Laura M. et al. (1999) "The Arp2/3 complex: a multifunctional actin organizer" *Current Opinion in Cell Biology* 11:117–121.
Machesky, Laura M. et al. (1997) "Mammalian actin–related protein 2/3 complex localizes to regions of lamellipodial protrusion and is composed of evolutionarily conserved proteins" *Biochem. J.* 328:105–112.
Machesky, Laura M. et al. (1999) "Scar, a WASP–related protein, activates nucleation of actin filaments by the Arp2/3 complex" *Proc. Natl. Acad. Sci. USA* 96:3739–3744.
Machesky, Laura M. et al. (1998) "Scar1 and the related Wiskott–Aldrich syndrome protein, WASP, regulate the actin cytoskeleton through the Arp2/3 complex" *Current Biology* 8:1347–56.
Miki, Hiroaki et al. (1996) "N–WASP, a novel actin–depolymerizing protein, regulates the cortical cytolkeletal rearrangement on a PIP2–dependent manner downstream of tyrosine kinases" *The EMBO Journal* 15(19):5326–35.
Miki, Hiroaki et al. (1998) "WAVE, a novel WASP–family protein involved in actin reorganization induced by Rac" *The EMBO Journal* 17(23):6932–41.
Mullins, R. Dyche (1998) "The interaction of Arp2/3 complex with actin: Nucleation, high affinity pointed end capping, and formation of branching networks of filaments" *Proc. Natl. Acad. Sci. USA* 95:6181–86.
Nagase, Takahiro et al. (1996) Prediction of the Coding Sequences of Unidentified Human Genes. VI. The Coding Sequences of 80 New Genes (KIAA0201–KIAA0280) Deduced by Analysis of cDNA Clones from Cell Line KG–1 and Brain *DNA Research* 3:321–329.
Ramesh Narayanaswamy et al. (1999) "Waltzing with WASP" *Trends in Cell Biology* 9:15–19.
Saxe, Charles L. (1999) "INSIGHTS FROM MODEL SYSTEMS. Learning from the Slime Mold:*Dictyostelium* and Human Disease" *AM. J. Hum. Genet.* 65:25–30.
Suetsugu, Shiro et al. (1999) "Identification of Two Human WAVE/SCAR Homologues as General Actin Regulatory Molecules Which Associate with the Arp2/3 Complex" *Biochemical and Biophysical Research Communications* 260:296–302.

* cited by examiner

*Primary Examiner*—Kenneth R. Horlick
*Assistant Examiner*—Cynthia Wilder
(74) *Attorney, Agent, or Firm*—Bill T. Brazil

(57) ABSTRACT

The present invention relates, at least in part, to polypeptides which include Bcl-xL binding domains, novel Bcl-xL binding domains of Pablo polypeptides, nucleic acid molecules encoding such polypeptides, and uses thereof. For example, such polypeptides and nucleic acid molecules are useful in modulating apoptosis, particularly in neural cells, as well as in the treatment or prevention of disorders that can benefit from modulation of cell death.

8 Claims, 17 Drawing Sheets values are the mean ± SD; n=4; *p<0.01

OGN cultures 34 hr. post-transfection

PC12 cells approx. 24 hr. post-transfection rat hippocampal cultures 30 hr. post-transfection HEK 293: 48 hr. post-transfection

FIG. 10A

Bclxl (ΔTM)/pAS-1

| | 10 | 20 | 30 | 40 | 50 |
|---|---|---|---|---|---|
| 19 Bclxl/pAS2-1 | CAGCTTTGAC | TCATATGAAA | ATGTCTCAGA | GCAACCGGGA | GCTGGTGGTT |
| | 60 | 70 | 80 | 90 | 100 |
| 19 Bclxl/pAS2-1 | GACTTTCTCT | CCTACAAGCT | TTCCCAGAAA | GGATACAGCT | GGAGTCAGTT |
| | 110 | 120 | 130 | 140 | 150 |
| 19 Bclxl/pAS2-1 | TAGTGATGTG | GAAGAGAACA | GGACTGAGGC | CCCAGAAGGG | ACTGAATCGG |
| | 160 | 170 | 180 | 190 | 200 |
| 19 Bclxl/pAS2-1 | AGATGGAGAC | CCCCAGTGCC | ATCAATGGCA | ACCCATCCTG | GCACCTGGCA |
| | 210 | 220 | 230 | 240 | 250 |
| 19 Bclxl/pAS2-1 | GACAGCCCCG | CGGTGAATGG | AGCCACTGGC | CACAGCAGCA | GTTTGGATGC |

FIG. 10B

| | 260 | 270 | 280 | 290 | 300 |
|---|---|---|---|---|---|
| 19 Bclxl/pAS2-1 | CCGGGAGGTG | ATCCCCATGG | CAGCAGTAAA | GCAAGCGCTG | AGGGAGGCAG |
| | 310 | 320 | 330 | 340 | 350 |
| 19 Bclxl/pAS2-1 | GCGACGAGTT | TGAACTGCGG | TACCGGCGGG | CATTCAGTGA | CCTGACATCC |
| | 360 | 370 | 380 | 390 | 300 |
| 19 Bclxl/pAS2-1 | CAGCTCCACA | TCACCCCAGG | GACAGCATAT | CAGAGCTTTG | AACAGGTAGT |
| | 410 | 420 | 430 | 440 | 450 |
| 19 Bclxl/pAS2-1 | GAATGAACTC | TTCCGGGATG | GGGTAAACTG | GGGTCGCATT | GTGGCCTTTT |
| | 460 | 470 | 480 | 490 | 500 |
| 19 Bclxl/pAS2-1 | TCTCCTTCGG | CGGGGCACTG | TGCGTGGAAA | GCGTAGACAA | GGAGATGCAG |

FIG. 10C

| | 510 | 520 | 530 | 540 | 550 |
|---|---|---|---|---|---|
| 19 Bclx1/pAS2-1 | GTATTGGTGA | GTCGGATCGC | AGCTTGGATG | GCCACTTACC | GGAATGACCA |
| | 560 | 570 | 580 | 590 | 600 |
| 19 Bclx1/pAS2-1 | CCTAGAGCCT | TGGATCCAGG | AGAACGGCGG | CTGGGATACT | TTTGTGGAAC |
| | 610 | 620 | 630 | 640 | 650 |
| 19 Bclx1/pAS2-1 | TCTATGGGAA | CAATGCAGCA | GCCGAGAGCC | GAAAGGGCCA | GGAACGCTTC |
| | 660 | 670 | 680 | 690 | 700 |
| 19 Bclx1/pAS2-1 | AACCGCTGAG | TCGACCTGCA | GCCAAGCTAA | TTCCGGGCGA | ATTTCTTATG |
| | 710 | 720 | 730 | 740 | 750 |
| 19 Bclx1/pAS2-1 | ATTTATGATT | TTTATTATTA | AATAAGTTAT | AAAAAAAATA | AGTGTAT |

FIG. 11

Amino Acid Sequence of Bclxl (TM)
Used As Bait In Yeast 2-Hybrid Screen.

```
         10        20        30        40        50        60        70
MSQSNRELVVDFLSYKLSQKGYSWSQFSDVEENRTEAPEGTESEMETPSAINGNPSWHLADSPAVNGATA      70
HSSSLDAREVIPMAAVKQALREAGDEFELRYRRAFSDLTSQLHITPGTAYQSFEQVVNELFRDGVNWGRI     140
VAFFSFGGALCVESVDKEMQVLVSRIAAWMATYLNDHLEPWIQENGGWDTFVELYGNNAAAESRKGQERF     210
NR                                                                        212
```

FIG. 12A

Nucleotide Sequence of Pablo D142

```
         10        20        30        40        50        60        70
atgccgctagtgaaagaaacatcgatcctagcgcacttgtgccacacagcactgcctagaggcattaaga      70
atgaactggaatgtgtaaccaatatattcctgcaaataattagacaactaagtagcctagtaata         140
tgctgaagatatatttggagaattattcaatgaagcacatagtttcttcagagtcaactcattgcaa        210
gaacgtgtgaccgtttatctgttagtgttacacagcttgatcacacagagaagaaattgtctttgcaag      280
atataacaatgaggaaagctttcgaagttctacaattcaagaccagcagctttcgatcgcaagactttt     350

360       370       380       390       400       410       420
gcctattccattacaggagacgtacgatgtttgtgaacagcctccacctctcaatatactcactccttat    420
agagatgatggtaaagaaggtctgaagtttatataccaatcctcgtatttcttgatctatggaaagaaa     490
aaatgttgcaagatacagagaggataaagaggaagcagaagcagaaaatctagatcgtcc               560
tcatgaaccagaaagagtgccaagagcacctcatgacagcggcgagaatggcagaagctgccaaggt      630
ccagagctggctgaagatgctaatctcttacataagcatattgaagttgctaatgcccagcctctc         700

710       720       730       740       750       760       770
atttgaaacaagacctcagacatcagacatacgtggatcatatggatcttactcactttctgccttgccatt   770
tagtcagatgagtgagcttctgactagagctgaggaaaggtattagtcagaccacatgaaccacctcca      840
cctccaccaatgcatgagcaggagaggatgcaaaaaaccgataccacctgtatcagttctgctacaggtttga    910
tagaaaatcgccctcagtcagtgacacaccagcagaacacctgtgtttgtgagccccactccccacctcc      980
tccaccacctcttccatctgcctttgtcaactctgccttgtcaacttccattcctcattaagagcttcaatgactcctcaacttcaactctcccct 1050
```

FIG. 12B

```
         1060      1070      1080      1090      1100      1110      1120
ccagtacctcccccacctccacctccagcaccactgctttgcaagctccagcagtaccaccacctccagctc    1120
ctcttcagattgcccctggagttcttcacccagctcctccaattgcacctcctctagtacagccctc        1190
tccaccagtagctagagctgccccagtatgtgagactgtaccagttcatcatccactcccacaaggt        1254
```

FIG. 13

Amino Acid Sequence of Pablo Δ142

|  | 10 | 20 | 30 | 40 |  |
|---|---|---|---|---|---|
| MPLVKRNIDPRHLCHTALPRGIKNELECVTNISLANIIRQ | | | | | 40 |
| LSSLSKYAEDIFGELFNEAHSFSFRVNSLQERVDRLSVSV | | | | | 80 |
| TQLDPKEEELSLQDITMRKAFRSSTIQDQQLFDRKTLPIP | | | | | 120 |
| LQETYDVCEQPPPLNILTPYRDDGKEGLKFYTNPSYFFDL | | | | | 160 |
| WKEKMLQDTEDKRKEKRKQKQKNLDRPHEPEKVPRAPHDR | | | | | 200 |

|  | 210 | 220 | 230 | 240 |  |
|---|---|---|---|---|---|
| RREWQKLAQGPELAEDDANLLHKHIEVANGPASHFETRPQ | | | | | 240 |
| TYVDHMDGSYSLSALPFSQMSELLTRAEERVLVRPHEPPP | | | | | 280 |
| PPPMHGAGDAKPIPTCISSATGLIENRPQSPATGRTPVFV | | | | | 320 |
| SPTPPPPPPPLPSALSTSSLRASMTSTPPPPVPPPPPPPA | | | | | 360 |
| TALQAPAVPPPPAPLQIAPGVLHPAPPPIAPPLVQPSPPV | | | | | 400 |

|  | 410 | 420 | 430 | 440 |  |
|---|---|---|---|---|---|
| ARAAPVCETVPVHPLPQG | | | | | 418 |

PABLO, A POLYPEPTIDE THAT INTERACTS WITH BCL-XL, AND USES RELATED THERETO

This application is a divisional of U.S. application Ser. No. 09/425,501, filed on Oct. 22, 1999, the entire disclosure of which is hereby incorporated by reference.

BACKGROUND OF THE INVENTION

Apoptosis has been implicated in controlling the amount and distribution of certain differentiated cell types, such as cells of the hematopoietic lineage, as well as other somatic and germ cells. Apoptosis was first described as a morphologic pattern of cell death characterized by cell shrinkage, membrane blebbing and chromatin condensation culminating in cell fragmentation (Kerr et al., 1972, *Br. J. Cancer* 26:239). Cells undergoing apoptosis display a characteristic pattern of internucleosomal DNA cleavage (Wyllie, 1980, *Int. Rev. Cytol.* 69:251; Abrams et al., 1993, *Development* 117:29).

The first gene to be identified which encoded a protein involved in modulating apoptosis, bcl-2, was cloned from the chromosomal breakpoint of t(14;18)-bearing B-cell lymphomas (Tsujimoto et al., 1984, *Science* 226:1097) and shown to inhibit cellular susceptibility to apoptosis (Cory, 1994, *Philos. Trans. R. Soc. Lond. B. Biol. Sci.* 345: 289). Several genes with homology to bcl-2 have subsequently been characterized, including the following: a1, which encodes an 80-amino acid protein that is rapidly induced in macrophages in response to GM-CSF or LPS (Lin et al., 1993, *J. Immunol.* 151: 1979–1988); mcl-1, an early response gene in myeloid cell lines which undergo macrophage differentiation (Kozopas et al., 1993, *Proc. Natl. Acad. Sci. USA* 90: 3516–3520); and bak, a bcl-2 homologue that may enhance apoptosis (Chittenden et al., 1995, *Nature* 374:733; Kiefer et al., 1995, *Nature* 374:736). Other proteins which interact with and/or are structurally related to the bcl-2 gene product have also been identified, such as for example, Bcl-xL and Bcl-xS (Boise et al., 1993, *Cell* 74:597); Ced-9 (Vaux et al., 1992, *Science* 258:1955) and two DNA virus proteins, LMW5-HL and BHRF-1 of the Epstein Barr virus.

The bcl-x gene product, closely related to the Bcl-2 protein family, also protects cells from apoptosis. Analysis of mice deficient in Bcl-x suggests that it supports the viability of immature cells during development of the nervous and hematopoietic systems (Motoyama et al., 1995, *Science* 267: 1506–1510; Ma et al., 1995. *Proc. Natl. Acad. Sci. USA* 92: 4763–4767). Alternative splicing of human bcl-x may result in at least two distinct bcl-x mRNA species, bcl-xL and bcl-xS. The predominant protein product (233 amino acids) of the larger bcl-x mRNA, Bcl-xL, inhibits cell death upon growth factor withdrawal (Boise et al., 1993. *Cell* 74, 597–608) and its transgenic expression alters thymocyte maturation leading to increased numbers of mature thymocytes (Chao et al., 1995, *J. Exp. Med.* 182: 821–828; Grillot et al., 1995, *J. Exp. Med.* 182: 1973–1983). Bcl-xS, on the other hand, inhibits the ability of Bcl-2 to inhibit cell death and renders cells more susceptible to apoptotic cell death. Additional murine Bcl-x isoforms, termed Bcl-xβ and Bcl-xΔTM, have been identified. The β isoform may inhibit apoptosis in neurons (Gonzalez-Garcia et al., 1995, *Proc. Natl. Acad. Sci. U.S.A.* 92: 4304–4308) and the ΔTM isoform may inhibit apoptosis in B-cells (Fang et al., supra).

The BCL-2 family of proteins is thus comprised of pro-apoptotic as well as anti-apoptotic members (Farrow and Brown, 1996, *Curr. Opin. Genet. Dev.* 6:45). Bcl-2-related proteins share homology clustered within four conserved regions termed Bcl-2 homology 1 through 4 (BH1–4) domains. An amphipathic alpha helix, BH3, is of particular importance for the proapoptotic family members (Korsmeyer, 1999, *Cancer Res.* 1: 1693s–1700s; Chittenden et al., 1995, *EMBO J.* 14: 5589). Proapoptotic molecules bear sequence homology to the Bcl-2 family only at BH3. A hydrophobic cleft formed by the BH1, BH2 and BH3 domains of Bcl-xL is responsible for interactions between Bcl-xL and BH3 -containing death agonists (Minn et al., *EMBO J.* 1999, 18 (3): 632–43).

In addition to playing a role in normal development, apoptosis has been implicated in pathologic conditions, such as Alzheimer's disease, Parkinson's disease, amyotrophic lateral sclerosis (ALS), and spinal muscular atrophy (see e.g., Passer et al., *J. Biol. Chem.* 1999, 274: 24007). Moreover, the ability to modulate apoptosis in cells would be valuable in controlling undesirable cell proliferation, e.g., the proliferation of cancer cells. Thus, the identification of agents that can modulate apoptosis may be useful in controlling cell proliferation, differentiation, and/or apoptosis in research and therapeutic applications.

SUMMARY OF THE INVENTION

The present invention is based, at least in part, on the discovery that Pablo and polypeptides derived therefrom interact with Bcl-xL and, therefore, are useful as modulating agents in regulating a variety of cellular processes, particularly in neural cell processes.

Accordingly, in one aspect, the present invention provides an isolated nucleic acid molecule comprising a nucleotide sequence encoding an isolated mammalian Bcl-xL binding domain, wherein said isolated mammalian Bcl-xL binding domain has 70% amino acid sequence identity with a Bcl-xL binding domain set forth in SEQ ID NO:2.

In another aspect, the invention provides an isolated nucleic acid molecule comprising a nucleotide sequence encoding an isolated mammalian Bcl-xL binding domain, wherein said nucleotide sequence hybridizes to the complement a nucleotide sequence set forth in SEQ ID NO:1 which encodes a Bcl-xL binding domain in 6×SSC at 45° C., followed by one or more washes in 0.2×SSC, 0.1% SDS at 50–65° C.

In one embodiment, the isolated Bcl-xL binding domain consists of amino acids 419–559 or amino acids 429–559 of SEQ ID NO:2. In another embodiment, the isolated mammalian Bcl-xL binding domain modulates apoptosis in a neural cell.

In one embodiment, the nucleic acid molecule is in a vector.

In one embodiment, the nucleic acid molecule comprises a naturally-occurring nucleotide sequence.

In one embodiment, the nucleic acid molecule encodes a fusion protein.

In another aspect, the invention provides an isolated nucleic acid molecule comprising a nucleotide sequence encoding a first polypeptide comprising a mammalian Bcl-xL binding domain, wherein said Bcl-xL binding domain has 70% amino acid sequence identity with a Bcl-xL binding domain set forth in SEQ ID NO:2 and a second peptide comprising non-Pablo a amino acid sequence.

In yet another aspect, the invention provides a polypeptide comprising an isolated mammalian Bcl-xL binding domain, wherein said isolated Bcl-xL binding domain consists of an amino acid sequence having at least 70% identity with a Pablo Bcl-xL binding domain shown in SEQ ID NO:2.

In still another embodiment, the invention provides a polypeptide comprising a Bcl-xL binding domain, wherein said Bcl-xL binding domain consists of an amino acid sequence having at least 70% identity with a Pablo Bcl-xL binding domain shown in SEQ ID NO:2, provided said polypeptide is not a full-length Pablo polypeptide.

In yet another aspect, the invention is directed to polypeptide comprising an isolated Bcl-xL binding domain set forth in SEQ ID NO:2.

In one embodiment, the invention is directed to a polypeptide in which a conservative amino acid substitution has been made.

In one aspect, the invention is drawn to a polypeptide consisting of an isolated Bcl-xL binding domain set forth in SEQ ID NO:2.

In one embodiment, the isolated Bcl-xL binding domain consists of amino acids 419–559 or amino acids 429–559.

In one embodiment, the isolated Bcl-xL binding domain modulates apoptosis in a neural cell.

In one aspect, the invention is directed to a fusion protein comprising a first polypeptide consisting of an isolated Bcl-xL binding domain and a second, non-Pablo polypeptide.

In yet another aspect, the invention is directed to an isolated nucleic acid molecule which is antisense to the portion of SEQ ID NO:1 which encodes a Bcl-xL binding domain.

In still another aspect, the invention is directed to a vector comprising a nucleic acid molecule of the invention. In one embodiment, such a vector is contained in a host cell.

In yet another aspect, the invention is directed to a neural cell line stably expressing a heterologous Pablo polypeptide or an isolated Bcl-xL binding domain set forth in SEQ ID NO:2.

In still another aspect, the invention is drawn to a non-human transgenic animal which contains cells carrying a nucleic acid molecule encoding an isolated mammalian Bcl-xL binding domain.

In yet another aspect, the invention is directed to a method of modulating apoptosis in a cell comprising modulating the activity of a Pablo polypeptide or Bcl-xL binding domain thereof.

In one embodiment, the step of modulating the activity of a Pablo polypeptide comprises modulating the interaction of a Bcl-xL binding domain with a Bcl-xL molecule.

The invention is further directed to a method of modulating apoptosis in a cell comprising modulating the expression of a Pablo polypeptide or Bcl-xL binding domain thereof.

In still another aspect, the invention is directed to a method for modulating Pablo activity in a cell comprising contacting the cell with an agent that modulates Pablo activity such that Pablo activity in the cell is modulated.

In yet another aspect, the invention is drawn to a method for modulating Pablo expression in a cell comprising contacting the cell with an agent that modulates Pablo expression such that Pablo expression in the cell is modulated.

In one embodiment, apoptosis is modulated in the cell.

In another embodiment, the cell is a neural cell.

In yet another aspect, the invention is directed to a method for treating a nervous system disorder in a subject comprising modulating the expression or activity of Pablo in a cell of the subject to thereby treat a nervous system disorder in the subject.

In another aspect, the invention is directed to a method for detecting the presence of Pablo in a cell comprising contacting the cell with an agent that detects expression or activity of Pablo thereby detecting Pablo in the cell.

In yet another aspect, the invention is drawn to a method for identifying a compound that modulates the pro-apoptotic activity of a Bcl-xL binding domain, comprising:

contacting a cell expressing a Bcl-xL binding domain with a test compound and;

determining the ability of the test compound to modulate the activity of a Bcl-xL binding domain to thereby identify a compound that modulates the pro-apoptotic activity of a Bcl-xL binding domain.

In still another aspect, the invention is directed to a method for identifying a compound that modulates the pro-apoptotic activity of a Bcl-xL binding domain, comprising:

contacting a cell-free mixture comprising a Bcl-xL binding domain with a test compound and;

determining the ability of the test compound to modulate the activity of a Bcl-xL binding domain to thereby identify a compound that modulates the pro-apoptotic activity of a Bcl-xL binding domain.

In one embodiment, the cell is a neural cell.

In another embodiment, the cell-free system comprises isolated mitochondria.

In one embodiment, the activity of a Bcl-xL binding domain is assayed by measuring the ability of the Bcl-xL binding domain to bind to Bcl-xL

BRIEF DESCRIPTION OF THE DRAWINGS

FIG. 10 shows the nucleotide sequence of the Bcl-xL ΔTM construct.

FIG. 11 shows the amino acid sequence of the Bcl-xL used as Bait in the yeast 2-hybrid screen.

FIG. 12 shows the nucleotide sequence of the Pablo Δ142 mutant.

FIG. 13 shows the amino acid sequence of the Pablo Δ142 mutant.

DETAILED DESCRIPTION OF THE INVENTION

Figure 1:
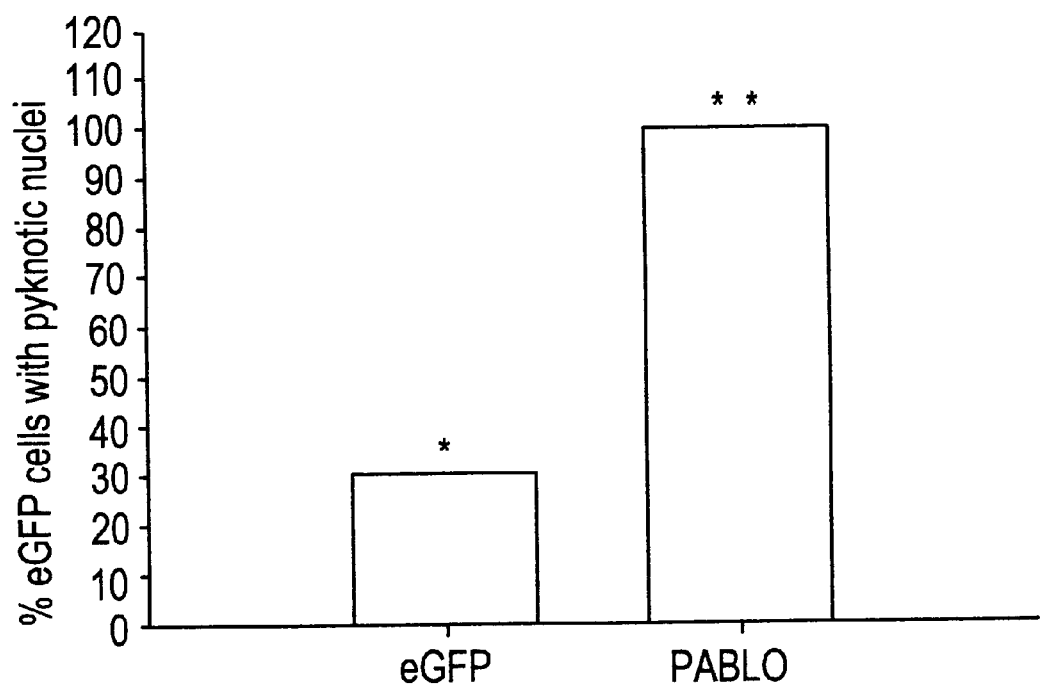
FIG. 1 demonstrates that at 30 hours post transfection, one hundred percent of rat hippocampal neurons transfected with Pablo displayed abnormal nuclear morphology as evidenced by pyknotic nuclei (**$p<0.01$) compared to cells transfected with empty vector (eGFP).

The present invention is based, at least in part, on the finding that the Pablo protein and novel polypeptides derived therefrom interact with Bcl-xL to modulate apoptosis, in particular neural cell apoptosis. A Pablo Bcl-xL binding domain has been characterized. Moreover, Pablo is the first pro-apoptotic polypeptide demonstrated to interact with Bcl-xL via a domain other than a BH3 domain.

These and other aspects of the invention are described in further detail in the following subsections:

I. Definitions

As used herein the term "Pablo" refers to pro-apoptotic Bcl-xL binding protein. The nucleotide and amino acid sequence of Pablo was previously identified by Nagase et al., (DNA Research (1996) 3:321–324) and referred to in that reference as KIAA0269. The nucleotide sequence of Pablo is set forth in SEQ ID NO:1 and the amino acid sequence of Pablo is set forth in SEQ ID NO:2. The Pablo polypeptide comprises a novel Bcl-xL binding domain having a Pablo activity. As used herein, the term "Pablo activity" or "activity of a Pablo polypeptide" includes the ability to modulate apoptosis in a cell, such as a neural cell. In one embodiment, a Pablo activity refers to an activity exerted by a Pablo polypeptide or portion thereof on a Pablo responsive cell or on a Pablo binding partner, as determined in vivo, or in vitro, according to standard techniques. In one embodiment, a Pablo activity is a direct activity, such as an association with a Pablo-target molecule. As used herein, a "target molecule" or "binding partner" is a molecule with which a Pablo protein binds or interacts in nature, such that Pablo-mediated function is achieved. Preferably, the binding partner with which a Pablo polypeptide interacts is a Bcl-xL molecule.

As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. As used herein, the term "modulating apoptosis" includes modulating programmed cell death in a cell, such as a neural cell. As used herein, the term "modulates apoptosis" includes either up regulation or down regulation of apoptosis in a cell. Modulation of apoptosis is discussed in more detail below and can be useful in ameliorating various disorders, e.g., neurological disorders.

As used herein, the term "Bcl-xL binding domain" includes a domain that interacts with a Bcl-xL polypeptide and preferably does not have significant amino acid sequence homology with a BH3 domain. A "BH3 domain" as used herein includes domains having the amino acid sequence Leu-Ala-Gln-Xaa$_1$-Gly-Asp-Xaa$_2$-Met-Asp, where Xaa$_1$ is Ile or Val and Xaa$_2$ is Gln or Ser, (see, e.g., U.S. Pat. No. 5,955,593). Preferred Bcl-xL binding domains are mammalian, e.g., human. Preferred Bcl-xL binding domains modulate apoptosis in a cell, preferably a neural cell. Bcl-xL binding domains can comprise about 50, 70, 90, 120, 130, 140, or 150 amino acids. It is believed that a minimum number of core amino acid residues are required for Bcl-xL binding, however, additional amino acid residues may be required for maximal Bcl-xL binding activity and may function e.g., by providing additional contact residues with a Bcl-xL polypeptide or by stabilizing a core Bcl-xL binding domain or by stabilizing the complex of a Bcl-xL binding domain with a Bcl-xL polypeptide. Preferred Bcl-xL binding domains are approximately 120–150 amino acid residues in length. More preferably, Bcl-xL binding domains are about 130–140 amino acids in length. A preferred Bcl-xL binding domain is set forth in SEQ ID NO:2. A preferred Bcl-xL binding domain is located at the carboxyl terminus of polypeptide, e.g., the polypeptide shown in SEQ. ID NO:2. A preferred Bcl-xL binding domain can comprise from about amino acid 420, 440, or 450, to about amino acid 470, 480, 500, 520, 540, or 560 of SEQ ID NO:2. Preferably, a Pablo Bcl-xL binding domain does not consist of amino acids 445–559 or amino acids 522–559 of SEQ ID NO:2. A particularly preferred Pablo Bcl-xL binding domain comprises from about amino acid 419 to about amino acid 559 or about amino acid 429 to about amino acid 559 of SEQ. ID NO:2. In another embodiment, a Pablo Bcl-xL binding domain comprises about amino acid 436 to about amino acid 483.

With respect to Bcl-xL binding domains, the term "isolated Bcl-xL binding domain" includes domains which are isolated or separated from the amino acid residues which comprise the full length Bcl-xL binding molecule, such as Pablo. For example, a nucleic acid molecule encoding an isolated Pablo Bcl-xL binding domain consists of that portion of a Pablo nucleic acid molecule encoding the Bcl-xL binding domain of a Pablo protein. Similarly, an isolated Pablo Bcl-xL binding domain consists of that portion of a Pablo polypeptide comprising the amino acid residues of the Bcl-xL binding domain. Such isolated Bcl-xL binding domains are separated from the remainder of the Pablo molecule from which they were derived (e.g., are separated from the amino terminal amino acids of the molecule or are separated from the nucleotides encoding the amino terminal amino acids of the molecule). Such isolated Bcl-xL binding domains and Pablo Bcl-xL binding domains can then be combined with or linked to additional nucleotide or amino acid sequences, e.g., vector sequences, or fusion proteins, etc.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived. For example, in various embodiments, the isolated Pablo nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" Pablo nucleic acid molecule may, however, be linked to other nucleotide sequences that do not normally flank the Pablo sequences in genomic DNA (e.g., the Pablo nucleotide sequences may be linked to vector sequences). In certain preferred embodiments, an "isolated" nucleic acid molecule, such as a cDNA molecule, also may be free of other cellular material. However, it is not necessary for the Pablo nucleic acid molecule to be free of other cellular material to be considered "isolated" (e.g., a Pablo DNA molecule separated from other mammalian DNA and inserted into a bacterial cell would still be considered to be "isolated").

As used herein, an "isolated protein" or "isolated polypeptide" refers to a protein or polypeptide that is substantially free of other proteins, polypeptides, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the Pablo protein is derived, or substantially free from chemical precursors or other chemicals when chemically synthesized. The language "substantially free of cellular material" includes preparations of Pablo protein in which the protein is separated from cellular components of the cells from which it is isolated or recombinantly produced. In one embodiment, the language "substantially free of cellular material" includes preparations of Pablo protein having less than about 30% (by dry weight) of non-Pablo protein (also referred to herein as a "contaminating protein"), more preferably less than about 20% of non-Pablo protein, still more preferably less than about 10% of non-Pablo protein, and most preferably less than about 5% non-Pablo protein. When the Pablo protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Pablo protein in which the protein is separated from chemical precursors or other chemicals which are involved in the synthesis of the protein. In one embodiment, the language "substantially free of chemical precursors or other chemicals" includes preparations of Pablo protein having less than about 30% (by dry weight) of chemical precursors or non-Pablo chemicals, more preferably less than about 20% chemical precursors or non-Pablo chemicals, still more preferably less than about 10% chemical precursors or non-Pablo chemicals, and most preferably less than about 5% chemical precursors or non-Pablo chemicals.

As used herein the term "neural cell" includes both nerve cells (i.e., neurons, e.g., uni-, bi-, or multipolar neurons) and neural cell precursors and glial cells (e.g., macroglia such as oligodendrocytes, Schwann cells, and astrocytes, or microglia) and glial cell precursors. In a preferred embodiment, the neural cells for use in the invention are mammalian, e.g., human cells, obtained from the central or peripheral nervous system. Neural precursor cells can also be used to practice the methods of the invention. As used herein, the term "neural precursor" refers to undifferentiated neural cells such as neural stem cells and neural progenitor cells. The term "neural stem cell" as used herein refers to an undifferentiated neural cell which is capable of proliferation and resulting in additional neural stem cells having the ability to differentiate into neural progenitor cells under appropriate conditions. The term "neural progenitor cell" as used herein refers to undifferentiated neural cells derived from neural stem cells and which under appropriate conditions differentiate into neural cells. The term "neural precursor" also includes totipotent cells (e.g., cells from early stage embryos which are unrestricted in their developmental capabilities) which are induced to differentiate into neural cells. Such precursor cells can be used as sources of the neural cells, i.e., the neural cells for use in the invention can be derived from such precursor cells. As used herein, the term "derived" (with respect to precursor cells) refers to cells which develop or differentiate from or have as ancestors totipotent stem cells and pluripotent stem cells. Methods of obtaining neural precursor cells e.g., neural stem cells and/or progenitor cells are known in the art. For example, neural stem cells and progenitor cells obtained as described in PCT publication WO 95/12665, published May 11, 1995; PCT Publication WO 97/02049, published Jan. 23, 1997; U.S. Pat. No. 5,753,506, the contents of which are incorporated herein by reference, can be used to generate cells for use in the present invention.

As used herein, the term "modulate Pablo activity or expression" includes up regulation and down regulation of a Pablo activity or Pablo expression (e.g., at the level of transcription or translation) in a cell.

The term "family" when referring to protein and nucleic acid molecules is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature. As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Preferably a host cell is a mammalian cell, e.g., a human cell. In particularly preferred embodiments, it is a neural cell.

As used herein, "heterologous DNA" or "heterologous nucleic acid" includes DNA that does not occur naturally as part of the genome in which it is present or which is found in a location or locations in the genome that differs from that in which it occurs in nature or which is operatively linked to DNA to which it is not normally linked in nature (i.e., a gene that has been operatively linked to a heterologous promoter). Heterologous DNA is not naturally occurring in that position or is not endogenous to the cell into which it is introduced, but has been obtained from another cell. Heterologous DNA can be from the same species or from a different species. In one embodiment, it is mammalian, e.g., human. DNA that one of skill in the art would recognize or consider as heterologous or foreign to the cell in which is expressed is herein encompassed by the term heterologous DNA.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, the term "antibody" is intended to include immunoglobulin molecules and immunologically active portions of immunoglobulin molecules, i.e., molecules that contain an antigen binding site which binds (immunoreacts with) an antigen, such as Fab and F(ab')$_2$ fragments, single chain antibodies, intracellular antibodies, scFv, Fd, or other fragments. Preferably, antibodies of the invention bind specifically or substantially specifically to Pablo molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used herein, the term "Pablo associated disorder" includes disorders that would benefit from the modulation of Pablo activity or expression. In one embodiment, Pablo associated disorders are disorders of the nervous system that would benefit from modulation of Pablo activity or expression. Examples of Pablo associated disorders include central or peripheral nervous system disorders which would benefit from an increase in cell death or a decrease in cell death. Exemplary disorders include acute and chronic neurodegenerative disorders, e.g., stroke, Alzheimer's disease, dementias related to Alzheimer's disease (such as Pick's disease), Parkinson's and other Lewy diffuse body diseases, Huntington's disease, spinal muscular atrophy, multiple sclerosis, amyotrophic lateral sclerosis, progressive supranuclear palsy, epilepsy, and Jakob-Creutzfieldt disease; psychiatric disorders, e.g., depression, schizophrenic disorders, korsakoffs psychosis, mania, anxiety disorders, or phobic disorders; learning or memory disorders, e.g., amnesia or age-related memory loss; and neurological disorders, e.g., migraine. Further examples of Pablo associated disorders include disorders involving unwanted cell proliferation, e.g., cancers, in particular, cancers of the central or peripheral nervous system.

II. Isolated Nucleic Acid Molecules Encoding Pablo or Portions Thereof

In practicing the methods of the invention, various agents can be used to modulate the activity and/or expression of Pablo in a cell. In one embodiment, an agent is a nucleic acid molecule encoding a Pablo polypeptide or a portion thereof. Such nucleic acid molecules are described in more detail below.

Analysis of the Pablo polypeptide has identified a region of the protein which mediates the interaction of Pablo with Bcl-xL in the C-terminal approximately 130 amino acids of the Pablo polypeptide. Accordingly, in one aspect, the invention pertains to nucleic acid molecules that encode a portion of a Pablo polypeptide that interacts with a Bcl-xL molecule.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp,D) | GAC, GAT |
| Cysteine (Cys, C) | TGC, TGT |
| Glutamic acid (Glu,E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe,F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a Pablo polypeptide of the invention (or a portion thereof) can be used to derive the Pablo amino acid sequence, using the genetic code to translate the DNA or RNA molecule into an amino acid sequence. Likewise, for any Pablo-amino acid sequence, corresponding nucleotide sequences that can encode Pablo protein can be deduced from the genetic code (which, because of its redundancy, will produce multiple nucleic acid sequences for any given amino acid sequence). Thus, description and/or disclosure herein of a Pablo nucleotide sequence should be considered to also include description and/or disclosure of the amino acid sequence encoded by the nucleotide sequence. Similarly, description and/or disclosure of a Pablo amino acid sequence herein should be considered to also include description and/or disclosure of all possible nucleotide sequences that can encode the amino acid sequence. One aspect of the invention pertains to isolated nucleic acid molecules that encode Pablo proteins or biologically active portions thereof, as well as nucleic acid fragments sufficient for use as hybridization probes to identify Pablo-encoding nucleic acids (e.g., Pablo mRNA) and fragments for use as PCR primers for the amplification or mutation of Pablo nucleic acid molecules. It will be understood that in discussing the uses of Pablo nucleic acid molecules, e.g., as shown in SEQ ID NO:1, that fragments of such nucleic acid molecules as well as full length Pablo nucleic acid molecules can be used. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid molecule having the nucleotide sequence of SEQ ID NO:1, or a portion thereof, can be isolated using standard molecular biology techniques and the sequence information provided herein. For example, using all or portion of the nucleic acid sequence of SEQ ID NO:1 as a hybridization probe, Pablo nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1 respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Pablo nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1.

In another preferred embodiment, an isolated nucleic acid molecule of the invention comprises a nucleic acid molecule which is a complement of the nucleotide sequence shown in SEQ ID NO:1 or a portion of any of these nucleotide sequences. A nucleic acid molecule which is complementary to the nucleotide sequence shown in SEQ ID NO:1 is one which is sufficiently complementary to the nucleotide sequence shown in SEQ ID NO:1 respectively, such that it can hybridize to the nucleotide sequence shown in SEQ ID NO:1 respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO:1 or a portion of any of this nucleotide sequences, e.g., the Bcl-xL binding domain encoded by SEQ ID NO:1.

Moreover, the nucleic acid molecule of the invention can comprise only a portion of the nucleic acid sequence of SEQ ID NO:1 for example a fragment which can be used as a probe or primer or a fragment encoding a biologically active portion of a Pablo protein. The nucleotide sequence determined from the cloning of the Pablo genes allows for the generation of probes and primers designed for use in identifying and/or cloning other Pablo family members, as well as Pablo family homologues from other species. The probe/primer typically comprises a substantially purified oligonucleotide. In one embodiment, the oligonucleotide comprises a region of nucleotide sequence that hybridizes under stringent conditions to at least about 12 or 15, preferably about 20 or 25, more preferably about 30, 35, 40, 45, 50, 55, 60, 65, 75, or 100 consecutive nucleotides of a sense sequence of SEQ ID NO:1 or of a naturally occurring allelic variant or mutant of SEQ ID NO:1. In another embodiment, a nucleic acid molecule of the present invention comprises a nucleotide sequence which is at least about 400, 450, 500, 550, 600, 650, 700, 750, 800, 900, 1000, or 1100 nucleotides in length and hybridizes under stringent hybridization conditions to a nucleic acid molecule of SEQ ID NO:1 or the complement thereof.

In another embodiment, a nucleic acid molecule of the invention comprises at least about 100, 200, 300, 400, 500, 600, 700, 800, 900, 1000, or 1100 contiguous nucleotides of SEQ ID NO:1.

In other embodiments, a nucleic acid molecule of the invention has at least 70% identity, more preferably 80% identity, and even more preferably 90% identity with a nucleic acid molecule comprising: at least about 300, 400, 500, 600, 700, 800, or at about 900 nucleotides of SEQ ID NO:1.

Probes based on the Pablo nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues, particularly neural cells or tissues, particularly neural cells or tissues, which misexpress a Pablo protein, such as by measuring a level of a Pablo-encoding nucleic acid in a sample of cells from a subject e.g., detecting Pablo mRNA levels or determining whether a genomic Pablo gene has been mutated or deleted.

A nucleic acid fragment encoding a "biologically active portion of a Pablo protein" can be prepared by isolating a portion of the nucleotide sequence of SEQ ID NO:1 which encodes a polypeptide having a Pablo biological activity (e.g., the ability to bind to Bcl-xL), expressing the encoded portion of the Pablo protein (e.g., by recombinant expression in vitro) and assessing the activity of the encoded portion of the Pablo protein.

Nucleic acid molecules that differ from SEQ ID NO:1 due to degeneracy of the genetic code, and thus encode the same Pablo protein as that encoded by SEQ ID NO:1 are encompassed by the invention. Accordingly, in another embodiment, an isolated nucleic acid molecule of the invention has a nucleotide sequence encoding a protein having an amino acid sequence shown in SEQ ID NO:2.

In addition to the Pablo nucleotide sequence shown in SEQ ID NO:1, it will be appreciated by those skilled in the art that DNA sequence polymorphisms that lead to changes in the amino acid sequences of the Pablo proteins may exist within a population (e.g., the human population). Such genetic polymorphism in the Pablo genes may exist among individuals within a population due to natural allelic variation. As used herein, the terms "gene" and "recombinant gene" refer to nucleic acid molecules which include an open reading frame encoding a Pablo protein, preferably a mammalian Pablo protein, and can further include non-coding regulatory sequences, and introns. Such natural allelic variations include both functional and non-functional Pablo proteins and can typically result in 1–5% variance in the nucleotide sequence of a Pablo gene. Any and all such nucleotide variations and resulting amino acid polymorphisms in Pablo genes that are the result of natural allelic variation and that do not alter the functional activity of a Pablo protein are intended to be within the scope of the invention.

Moreover, nucleic acid molecules encoding other Pablo family members and, thus, which have a nucleotide sequence which differs from the Pablo family sequence of SEQ ID NO:1 are intended to be within the scope of the invention. Moreover, nucleic acid molecules encoding Pablo proteins from different species, and thus which have a nucleotide sequence which differs from the Pablo sequence of SEQ ID NO:1 are intended to be within the scope of the invention.

Nucleic acid molecules corresponding to natural allelic variants and homologues of the Pablo molecules of the invention can be isolated, e.g., based on their homology to the Pablo nucleic acids disclosed herein using the cDNAs disclosed herein, or portions thereof, as a hybridization probe according to standard hybridization techniques. For example, a Pablo DNA can be isolated from a human genomic DNA library using all or portion of SEQ ID NO:1 as a hybridization probe and standard hybridization techniques (e.g., as described in Sambrook, J., et al. *Molecular Cloning: A Laboratory Manual.* 2nd, ed., Cold Spring Harbor Laboratory, Cold Spring Harbor, N.Y., 1989). Moreover, a nucleic acid molecule encompassing all or a portion of a Pablo gene can be isolated by the polymerase chain reaction using oligonucleotide primers designed based upon the sequence of SEQ ID NO:1. For example, mRNA can be isolated from cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1. A nucleic acid molecule of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a Pablo nucleotide sequence can be prepared by standard synthetic techniques, e.g., using an automated DNA synthesizer.

In another embodiment, an isolated nucleic acid molecule of the invention can be identified based on shared nucleotide sequence identity using a mathematical algorithm. Such algorithms are outlined in more detail below (see, e.g., section III).

In another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or its complement. In other embodiment, the nucleic acid molecule is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 or its complement corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). In addition to the Pablo nucleotide sequences shown in SEQ ID NO: 1 it will be appreciated by those skilled in the art that DNA sequence polymorphisms that lead to minor changes in the nucleotide or amino acid sequences of a Pablo may exist within a population. Such genetic polymorphism in a Pablo gene may exist among individuals within a population due to natural allelic variation. Such natural allelic variations can typically result in 1–2% variance in the nucleotide sequence of the gene. Such nucleotide variations and resulting amino acid polymorphisms in a Pablo that are the result of natural allelic variation and that do not alter the functional activity of a Pablo polypeptide are within the scope of the invention.

In addition to naturally-occurring allelic variants of Pablo sequences that may exist in the population, the skilled artisan will further appreciate that minor changes may be introduced by mutation into nucleotide sequences, e.g., of SEQ ID NO:1, thereby leading to changes in the amino acid sequence of the encoded protein, without altering the functional activity of a Pablo protein. For example, nucleotide substitutions leading to amino acid substitutions at "non-essential" amino acid residues may be made in the sequence of SEQ ID NO: 1. A "non-essential" amino acid residue is a residue that can be altered from the wild-type sequence of a Pablo nucleic acid molecule (e.g., the sequence of SEQ ID NO: 1) without altering the functional activity of a Pablo molecule. Exemplary residues which are non-essential and, therefore, amenable to substitution, can be identified by one of ordinary skill in the art by performing an amino acid alignment of Pablo-related molecules and determining residues that are not conserved. Such residues, because they have not been conserved, are more likely amenable to substitution.

Accordingly, another aspect of the invention pertains to nucleic acid molecules encoding Pablo proteins that contain changes in amino acid residues that are not essential for a Pablo activity. Such Pablo proteins differ in amino acid sequence from SEQ ID NO: 2 yet retain an inherent Pablo activity. An isolated nucleic acid molecule encoding a non-natural variant of a Pablo protein can be created by introducing one or more nucleotide substitutions, additions or deletions into the nucleotide sequence of SEQ ID NO: 1 such that one or more amino acid substitutions, additions or deletions are introduced into the encoded protein. Mutations can be introduced into SEQ ID NO: 1 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a Pablo is preferably replaced with another amino acid residue from the same side chain family.

Alternatively, in another embodiment, mutations can be introduced randomly along all or part of a Pablo coding sequence, such as by saturation mutagenesis, and the resultant mutants can be screened for their ability to bind to DNA and/or activate transcription, to identify mutants that retain functional activity. Following mutagenesis, the encoded a Pablo mutant protein can be expressed recombinantly in a host cell and the functional activity of the mutant protein can be determined using assays available in the art for assessing a Pablo activity.

Yet another aspect of the invention pertains to isolated nucleic acid molecules encoding a Pablo fusion proteins. Such nucleic acid molecules, comprising at least a first nucleotide sequence encoding a full-length Pablo protein, polypeptide or peptide having a Pablo activity operatively linked to a second nucleotide sequence encoding a non-Pablo protein, polypeptide or peptide, can be prepared by standard recombinant DNA techniques.

In a preferred embodiment, a mutant Pablo protein can be assayed for the ability to: 1) bind to Bcl-xL and/or 2) modulate apoptosis, preferably in a neural cell, e.g., a cell of the central or peripheral nervous system.

In addition to the nucleic acid molecules encoding Pablo proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Pablo coding strand, or only to a portion thereof. In one embodiment, an antisense nucleic acid molecule is antisense to a "coding region" of the coding strand of a nucleotide sequence encoding Pablo. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Pablo. The term "noncoding region" refers to 5' and 3' sequences which flank the coding region that are not translated into amino acids (i.e., also referred to as 5' and 3' untranslated regions).

Given the coding strand sequences encoding Pablo disclosed herein, antisense nucleic acids of the invention can be designed according to the rules of Watson and Crick base pairing. The antisense nucleic acid molecule can be complementary to the entire coding region of Pablo mRNA, but more preferably is an oligonucleotide which is antisense to only a portion of the coding or noncoding region of Pablo mRNA. For example, the antisense oligonucleotide can be complementary to the region surrounding the translation start site of Pablo mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a Pablo protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res*. 15:6131–6148) or a chimeric RNA-DNA analogue (Inoue et al. (1987) *FEBS Lett*. 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave Pablo mRNA transcripts to thereby inhibit translation of Pablo mRNA. A ribozyme having specificity for a Pablo-encoding nucleic acid can be designed based upon the nucleotide sequence of SEQ ID NO:1. For example, a derivative of a Tetrahymena L-19 IVS RNA can be constructed in which the nucleotide sequence of the active site is complementary to the nucleotide sequence to be cleaved in a Pablo-encoding mRNA. See, e.g., Cech et al. U.S. Pat. No. 4,987,071; and Cech et al. U.S. Pat. No. 5,116,742. Alternatively, Pablo mRNA can be used to select a catalytic RNA having a specific ribonuclease activity from a pool of RNA molecules. See, e.g., Bartel, D. and Szostak, J. W. (1993) *Science* 261:1411–1418.

Alternatively, gene expression can be inhibited by targeting nucleotide sequences complementary to the regulatory region of Pablo (e.g., the Pablo promoter and/or enhancers) to form triple helical structures that prevent transcription of the Pablo gene in target cells. See generally, Helene, C. (1991) *Anticancer Drug Des*. 6(6):569–84; Helene, C. et al. (1992) *Ann. N. Y. Acad Sci*. 660:27–36; and Maher, L. J. (1992) *Bioassays* 14(12):807–15.

In yet another embodiment, the Pablo nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of Pablo nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of Pablo nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of Pablo can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Pablo nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

III. Isolated Pablo Proteins, Fragments Thereof, and Anti-Pablo Antibodies

One aspect of the invention pertains to isolated Pablo proteins, and biologically active portions thereof, as well as polypeptide fragments suitable for use as immunogens to raise anti-Pablo antibodies. In one embodiment, native -Pablo proteins can be isolated from cells or tissue sources by an appropriate purification scheme using standard protein purification techniques. In another embodiment, Pablo proteins are produced by recombinant DNA techniques. Alternative to recombinant expression, a Pablo protein or polypeptide can be synthesized chemically using standard peptide synthesis techniques. It will be understood that in discussing the uses of Pablo proteins, e.g., as shown in SEQ ID NO:2, that fragments of such proteins that are not full length Pablo polypeptides, e.g., the Bcl-xL binding domain set forth in SEQ ID NO:2, as well as full length Pablo proteins can be used.

Another aspect of the invention pertains to isolated Pablo proteins. Preferably, the Pablo proteins comprise the amino acid sequence encoded by SEQ ID NO:1 or a portion thereof. In another preferred embodiment, the protein comprises the amino acid sequence of SEQ ID NO: 2 or a portion thereof. In other embodiments, the protein has at least 50%, at least 60% amino acid identity, more preferably 70% amino acid identity, more preferably 80%, and even more preferably, 90% or 95% amino acid identity with the amino acid sequence shown in SEQ ID NO: 2 or a portion thereof, e.g., the Bcl-xL binding domain set forth in SEQ ID NO:2. Preferred portions of Pablo polypeptide molecules are biologically active, i.e., encode a portion of the Pablo polypeptide having the ability to bind to Bcl-xL and/or modulate apoptosis in a cell, preferably a neural cell, e.g., a cell of the central or peripheral nervous system.

Biologically active portions of a Pablo protein include peptides comprising amino acid sequences sufficiently homologous to or derived from the amino acid sequence of the Pablo protein, which include less amino acids than the full length Pablo proteins, and exhibit at least one activity of a Pablo protein.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions× 100). The percent identity between the two sequences is a function of the number of identical positions shared by the sequences, taking into account the number of gaps, and the length of each gap, which are introduced for optimal alignment of the two sequences. As used herein amino acid or nucleic acid "identity" is equivalent to amino acid or nucleic acid "homology".

The comparison of sequences and determination of percent identity between two sequences can be accomplished using a mathematical algorithm. A non-limiting example of a mathematical algorithm utilized for comparison of sequences is the algorithm of Karlin and Altschul (1990) Proc. Natl. Acad. Sci. USA 87:2264, modified as in Karlin and Altschul (1993) Proc. Natl. Acad. Sci. USA 90:5873. Such an algorithm is incorporated into the NBLAST and XBLAST programs (version 2.0) of Altschul, et al. (1990) J. Mol. Biol. 215:403. BLAST nucleotide searches can be performed with the NBLAST program score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Research 25(17):3389. When utilizing BLAST and Gapped BLAST programs, the default parameters of the respective programs (e.g., XBLAST and NBLAST) can be used. Another preferred, non-limiting algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Another non-limiting example of a mathematical algorithm utilized for the alignment of protein sequences is the Lipman-Pearson algorithm (Lipman and Pearson (1985) Science 227:1435). When using the Lipman-Pearson algorithm, a PAM250 weight residue table, a gap length penalty of 12, a gap penalty of 4, and a Kutple of 2 can be used. A preferred, non-limiting example of a mathematical algorithm utilized for the alignment of nucleic acid sequences is the Wilbur-Lipman algorithm (Wilbur and Lipman (1983) Proc. Natl. Acad. Sci. USA 80:726). When using the Wilbur-Lipman algorithm, a window of 20, gap penalty of 3, Ktuple of 3 can be used. Both the Lipman-Pearson algorithm and the Wilbur-Lipman algorithm are incorporated, for example, into the MEGALIGN program (e.g., version 3.1.7) which is part of the DNASTAR sequence analysis software package.

Additional algorithms for sequence analysis are known in the art, and include ADVANCE and ADAM., described in Torelli and Robotti (1994) Comput. Appl. Biosci. 10:3; and FASTA, described in Pearson and Lipman (1988) *PNAS* 85:2444.

In a preferred embodiment, the percent identity between two amino acid sequences is determined using the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna. CMP matrix and a gap weight of 40, 50, 60, 70, or 80 and a length weight of 1, 2, 3, 4, 5, or 6.

Protein alignments can also be made using the Geneworks global protein alignment program (e.g., version 2.5.1) with the cost to open gap set at 5, the cost to lengthen gap set at 5, the minimum diagonal length set at 4, the maximum diagonal offset set at 130, the consensus cutoff set at 50% and utilizing the Pam 250 matrix.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to Pablo nucleic acid molecules of the invention. BLAST protein searches can be performed with the XBLAST program, score=50, wordlength=3 to obtain amino acid sequences homologous to Pablo protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. For example, the nucleotide sequences of the invention can be analyzed using the default Blastn matrix 1–3 with gap penalties set at: existence 11 and extension 1. The amino acid sequences of the invention can be analyzed using the default settings: the Blosum62 matrix with gap penalties set at existence 11 and extension 1.

The invention also provides Pablo chimeric or fusion proteins. As used herein, a Pablo "chimeric protein" or "fusion protein" comprises a Pablo polypeptide operatively linked to a non-Pablo polypeptide. An "Pablo polypeptide" refers to a polypeptide having an amino acid sequence corresponding to Pablo polypeptide, whereas a "non-Pablo polypeptide" refers to a polypeptide having an amino acid sequence corresponding to a protein which is not substantially homologous to the Pablo protein, e.g., a protein which is different from the Pablo protein and which is derived from the same or a different organism. Within a Pablo fusion protein the Pablo polypeptide can correspond to all or a portion of a Pablo protein. In a preferred embodiment, a Pablo fusion protein comprises at least one biologically active portion of a Pablo protein, e.g., a Bcl-xL binding domain. Within the fusion protein, the term "operatively linked" is intended to indicate that the Pablo polypeptide and the non-Pablo polypeptide are fused in-frame to each other. The non-Pablo polypeptide can be fused to the N-terminus or C-terminus of the Pablo polypeptide.

For example, in one embodiment, the fusion protein is a GST-Pablo member fusion protein in which the Pablo member sequences are fused to the C-terminus of the GST sequences. In another embodiment, the fusion protein is a Pablo-HA fusion protein in which the Pablo member nucleotide sequence is inserted in a vector such as pCEP4-HA vector (Herrscher, R. F. et al. (1995) *Genes Dev.* 9:3067–3082) such that the Pablo member sequences are fused in frame to an influenza hemagglutinin epitope tag. Such fusion proteins can facilitate the purification of a recombinant Pablo member.

Fusion proteins and peptides produced by recombinant techniques may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a Pablo fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A Pablo encoding nucleic acid can be cloned into such an expression vector such that the fusion moiety is linked in-frame to the Pablo protein.

In another embodiment, the fusion protein is a Pablo protein containing a heterologous signal sequence at its N-terminus. In certain host cells (e.g., mammalian host cells), expression and/or secretion of Pablo can be increased through use of a heterologous signal sequence. The Pablo fusion proteins of the invention can be incorporated into pharmaceutical compositions and administered to a subject in vivo. Use of Pablo fusion proteins may be useful therapeutically for the treatment of disorders, e.g., cancer or Alzheimer's disease. Moreover, the Pablo-fusion proteins of the invention can be used as immunogens to produce anti-Pablo antibodies in a subject.

Preferably, a Pablo chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Pablo-encoding nucleic acid can be cloned into such an expression vector such that the fusion moiety is linked in-frame to the Pablo protein.

The present invention also pertains to variants of the Pablo proteins which function as either Pablo agonists (mimetics) or as Pablo antagonists. Variants of the Pablo proteins can be generated by mutagenesis, e.g., discrete point mutation or truncation of a Pablo protein. An agonist of the Pablo proteins can retain substantially the same, or a subset, of the biological activities of the naturally occurring form of a Pablo protein. An antagonist of a Pablo protein can inhibit one or more of the activities of the naturally occurring form of the Pablo protein by, for example, competitively modulating a cellular activity of a Pablo protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Pablo protein.

In one embodiment, the invention pertains to derivatives of Pablo which may be formed by modifying at least one amino acid residue of Pablo by oxidation, reduction, or other derivatization processes known in the art.

In one embodiment, variants of a Pablo protein which function as either Pablo agonists (mimetics) or as Pablo antagonists can be identified by screening combinatorial libraries of mutants, e.g., truncation mutants, of a Pablo protein for Pablo protein agonist or antagonist activity. In one embodiment, a variegated library of Pablo variants is generated by combinatorial mutagenesis at the nucleic acid level and is encoded by a variegated gene library. A variegated library of Pablo variants can be produced by, for example, enzymatically ligating a mixture of synthetic oligonucleotides into gene sequences such that a degenerate set of potential Pablo sequences is expressible as individual polypeptides, or alternatively, as a set of larger fusion proteins (e.g., for phage display) containing the set of Pablo sequences therein. There are a variety of methods which can be used to produce libraries of potential Pablo variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Pablo sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al (1984) *Science* 198:1056; Ike et al. (1983) *Nucleic Acid Res.* 11:477).

In addition, libraries of fragments of a Pablo protein coding sequence can be used to generate a variegated population of Pablo fragments for screening and subsequent selection of variants of a Pablo protein. In one embodiment, a library of coding sequence fragments can be generated by treating a double stranded PCR fragment of a Pablo coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal and internal fragments of various sizes of the Pablo protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Pablo proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Pablo variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated Pablo library. For example, a library of expression vectors can be transfected into a cell line which ordinarily synthesizes and secretes Pablo. The transfected cells are then cultured such that Pablo and a particular mutant Pablo are secreted and the effect of expression of the mutant on Pablo activity in cell supernatants can be detected, e.g., by any of a number of enzymatic assays. Plasmid DNA can then be recovered from the cells which score for inhibition, or alternatively, potentiation of Pablo activity, and the individual clones further characterized.

In addition to Pablo polypeptides consisting only of naturally-occurring amino acids, Pablo peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15: 29; Veber and Freidinger (1985) TINS p.392; and Evans et al. (1987) J. Med. Chem 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human Pablo, but have one or more peptide linkages optionally replaced by a linkage selected from the group consisting of: —CH2NH—, —CH2S—, —CH2—CH2—, —CH═CH— (cis and trans), —COCH2—, —CH(OH)CH2—, and —CH2SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—CH2NH—, CH2CH2—); Spatola, A. F. et al., Life Sci (1986) 38:1243–1249 (—CH2—S); Hann, M. M., J Chem Soc Perkin Trans I (1982) 307–314 (—CH—CH—, cis and trans); Almquist, R. G. et al., J Med Chem (1980) 23:1392–1398 (—COCH2—); Jennings-White, C. et al., Tetrahedron Lett (1982) 23:2533 (—COCH2—); Szelke, M. et al., European Appln. EP 45665 (1982) CA: 97:39405 (1982)(—CH(OH)CH2—); Holladay, M. W. et al., Tetrahedron Lett (1983) 24:4401–4404 (—C(OH)CH2—); and Hruby, V. J., Life Sci (1982) 31:189–199 (—CH2—S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a Pablo amino acid sequence with a D-amino acid of the same type (e.g., D-lysine in place of L-lysine) may be used to generate more stable peptides. In addition, constrained peptides comprising a Pablo amino acid sequence or a substantially identical sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

The amino acid sequences of Pablo polypeptides identified herein will enable those of skill in the art to produce polypeptides corresponding to Pablo peptide sequences and sequence variants thereof. Such polypeptides may be produced in prokaryotic or eukaryotic host cells by expression of polynucleotides encoding a Pablo peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:.501; Chaiken I. M. (1981) CRC Crit. Rev. Biochem. 11: 255; Kaiser et al. (1989) Science 243: 187; Merrifield, B. (1986) Science 232: 342; Kent, S. B. H. (1988) Ann. Rev. Biochem. 57: 957; and Offord, R. E. (1980) Semisynthetic Proteins, Wiley Publishing, which are incorporated herein by reference).

Peptides can be produced, typically by direct chemical synthesis, and used e.g., as agonists or antagonists of a Pablo/Pablo binding protein (e.g., Bcl-xL) interaction. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides may be used therapeutically to treat disease, e.g., by altering the process of apoptosis in a cell population of a patient.

An isolated Pablo protein, or a portion or fragment thereof, can also be used as an immunogen to generate antibodies that bind Pablo using standard techniques for polyclonal and monoclonal antibody preparation. A full-length Pablo protein can be used or, alternatively, the invention provides antigenic peptide fragments of Pablo for use as immunogens. The antigenic peptide of Pablo comprises at least 8 amino acid residues and encompasses an epitope of Pablo such that an antibody raised against the peptide forms a specific immune complex with Pablo. Preferably, the antigenic peptide comprises at least 10 amino acid residues, more preferably at least 15 amino acid residues, even more preferably at least 20 amino acid residues, and most preferably at least 30 amino acid residues.

Alternatively, an antigenic peptide fragment of a Pablo polypeptide can be used as the immunogen. An antigenic peptide fragment of a Pablo polypeptide typically comprises at least 8 amino acid residues of the amino acid sequence shown in SEQ ID NO: 2 and encompasses an epitope of a Pablo polypeptide such that an antibody raised against the peptide forms an immune complex with a Pablo molecule. Preferred epitopes encompassed by the antigenic peptide are regions of Pablo that are located on the surface of the protein, e.g., hydrophilic regions. In one embodiment, an antibody binds substantially specifically to a Pablo molecule. In another embodiment, an antibody binds specifically to a Pablo polypeptide.

Preferably, the antigenic peptide comprises at least about 10 amino acid residues, more preferably at least about 15 amino acid residues, even more preferably at least 20 about amino acid residues, and most preferably at least about 30 amino acid residues. Preferred epitopes encompassed by the antigenic peptide are regions of a Pablo polypeptide that are located on the surface of the protein, e.g., hydrophilic regions, and that are unique to a Pablo polypeptide. In one embodiment such epitopes can be specific for a Pablo proteins from one species, such as mouse or human (i.e., an antigenic peptide that spans a region of a Pablo polypeptide that is not conserved across species is used as immunogen; such non conserved residues can be determined using an alignment such as that provided herein). A standard hydrophobicity analysis of the protein can be performed to identify hydrophilic regions.

A Pablo immunogen typically is used to prepare antibodies by immunizing a suitable subject, (e.g., rabbit, goat, mouse or other mammal) with the immunogen. An appropriate immunogenic preparation can contain, for example, a recombinantly expressed Pablo protein or a chemically synthesized Pablo peptide. The preparation can further include an adjuvant, such as Freund's complete or incomplete adjuvant, or similar immunostimulatory agent. Immunization of a suitable subject with an immunogenic Pablo preparation induces a polyclonal anti-Pablo antibody response.

Accordingly, another aspect of the invention pertains to the use of anti-Pablo antibodies. Polyclonal anti-Pablo antibodies can be prepared as described above by immunizing a suitable subject with a Pablo immunogen. The anti-Pablo antibody titer in the immunized subject can be monitored over time by standard techniques, such as with an enzyme linked immunosorbent assay (ELISA) using immobilized a Pablo polypeptide. If desired, the antibody molecules directed against a Pablo polypeptide can be isolated from the mammal (e.g., from the blood) and further purified by well known techniques, such as protein A chromatography to obtain the IgG fraction. At an appropriate time after immunization, e.g., when the anti-Pablo antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a Pablo immunogen as described above, and the culture supernatants of the resulting hybridoma cells are screened to identify a hybridoma producing a monoclonal antibody that binds specifically to a Pablo polypeptide.

Any of the many well known protocols used for fusing lymphocytes and immortalized cell lines can be applied for the purpose of generating an anti-Pablo monoclonal antibody (see, e.g., G. Galfre et al. (1977) *Nature* 266:55052; Geifer et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 mycloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a Pablo molecule, e.g., using a standard ELISA assay.

As an alternative to preparing monoclonal antibody-secreting hybridomas, a monoclonal anti-Pablo antibody can be identified and isolated by screening a recombinant combinatorial immunoglobulin library (e.g., an antibody phage display library) with a Pablo to thereby isolate immunoglobulin library members that bind a Pablo polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J.* 12:725–734; Hawkins et al. (1992) *J Mol Biol* 25 226:889–896; Clarkson et al. (1991) *Nature* 352:624–628; Gram et al. (1992) *PNAS*

89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-Pablo antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhocyan et al. (1988) *Science* 15 239:1534; and Beidler et al. (1988) *J. Immunol.* 141:4053–4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable geneic display package and vectors containing nucleic acid molecules encoding a second polypeptide chain of a single binding pair member using techniques known in the art, e.g., as described in U.S. Pat. Nos. 5,565,332, 5,871,907, or 5,733,743.

An anti-Pablo antibody (e.g., monoclonal antibody) can be used to isolate a Pablo polypeptide by standard techniques, such as affinity chromatography or immunoprecipitation. Anti-Pablo antibodies can facilitate the purification of natural Pablo polypeptides from cells and of recombinantly produced Pablo polypeptides expressed in host cells. Moreover, an anti-Pablo antibody can be used to detect a Pablo protein (e.g., in a cellular lysate or cell supernatant). Detection may be facilitated by coupling (i.e., physically linking) the antibody to a detectable substance. Accordingly, in one embodiment, an anti-Pablo antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Anti-Pablo antibodies are also obtainable by a process comprising:
 (a) immunizing an animal with an immunogenic Pablo protein, or an immunogenic portion thereof unique to a Pablo polypeptide; and
 (b) isolating from the animal antibodies that specifically bind to a Pablo protein.

Accordingly, in one embodiment, anti-Pablo antibodies can be used, e.g., intracellularly to inhibit protein activity. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al. (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

In one embodiment, a recombinant expression vector is prepared which encodes the antibody chains in a form such that, upon introduction of the vector into a cell, the antibody chains are expressed as a functional antibody in an intracellular compartment of the cell. For inhibition of Pablo activity according to the inhibitory methods of the invention, an intracellular antibody that specifically binds the Pablo protein is expressed in the cytoplasm of the cell. To prepare an intracellular antibody expression vector, antibody light and heavy chain cDNAs encoding antibody chains specific for the target protein of interest, e.g., Pablo, are isolated, typically from a hybridoma that secretes a monoclonal antibody specific for the Pablo protein. Hybridomas secreting anti-Pablo monoclonal antibodies, or recombinant anti-Pablo monoclonal antibodies, can be prepared as described above. Once a monoclonal antibody specific for Pablo protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest*, Fifth Edition, U.S. Department of Health and Human Services, NIH Publication No. 91-3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., (Gly$_4$Ser)$_3$) and expressed as a single chain molecule. To inhibit Pablo activity in a cell, the expression vector encoding the anti-Pablo intracellular antibody is introduced into the cell by standard transfection methods, as discussed herein.

IV. Recombinant Expression Vectors and Host Cells

Another aspect of the invention pertains to vectors, preferably expression vectors, containing a nucleic acid encoding a Pablo protein (or a portion thereof). The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., Pablo proteins, mutant forms of Pablo proteins, fusion proteins, and the like).

The recombinant expression vectors of the invention can be designed for expression of Pablo proteins or protein fragments in prokaryotic or eukaryotic cells. For example, Pablo proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in Pablo activity assays, (e.g., direct assays or competitive assays described in detail below), or to generate antibodies specific for Pablo proteins, for example.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the Pablo expression vector is a yeast expression vector. Examples of vectors for expression in yeast *S. cerivisae* include pYepSec1 (Baldari, et al., (1987) *Embo J.* 6:229–234), pMFa (Kudjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corp, San Diego, Calif.).

Alternatively, Pablo proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banedji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Alternatively, a Pablo polypeptide can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, a nucleic acid molecule of the invention is expressed in mammalian cells using a mammalian expression vector. Examples of mammalian expression vectors include pMex-NeoI, pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, e.d. Nouer, L. , CRC, Boca Raton, Fla., pp167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Accordingly, in another embodiment, the invention provides a recombinant expression vector in which a Pablo DNA is operatively linked to an inducible eukaryotic promoter, thereby allowing for inducible expression of a Pablo protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Pablo mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a Pablo protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a Pablo protein or can be introduced on a separate vector. Cells stably transfected with the introduced nucleic acid can be identified by drug selection (e.g., cells that have incorporated the selectable marker gene will survive, while the other cells die).

In the case of neural cells which are stably transfected with Pablo, such lines can be made such that the Pablo gene is inducible, e.g., using the PC12 Tet-Off cell line (commercially available from Clontech; Palo Alto, Calif.). For example, the regulation of the expressed gene can be brought about by the double stable expression first of a "regulator" plasmid, which contains the tet-controlled trarnsactivator (tTA) and a second "response" plasmid, which contains Pablo, under the control of a promoter sequence that includes the tetracycline response element (TRE). The commercially avialable regulator plasmids are in vectors engineered for neomycin selection, necessitating that response vectors be constructed to include a second selectable marker. The construction of such cell lines is described in more detail in the appended Examples. Using such methods, Pablo expression can be turned off in the presence of an agent, e.g., tetracycline or a tetracycline-related compound (e.g., doxycycline) and turned on when the agent, e.g., tetracycline, is not added to the culture medium. Construction of this type of cell line permits the stable expression of Pablo in cells in which it is normally toxic.

A host cell of the invention, such as a prokaryotic or eukaryotic host cell in culture, can be used to produce (i.e., express) a Pablo protein. Accordingly, the invention further provides methods for producing a Pablo protein using the host cells of the invention. In one embodiment, the method comprises culturing the host cell of invention (into which a recombinant expression vector encoding a Pablo protein has been introduced) in a suitable medium such that a Pablo protein is produced. In another embodiment, the method further comprises isolating a Pablo protein from the medium or the host cell.

Certain host cells of the invention can also be used to produce non-human transgenic animals. For example, in one embodiment, a host cell of the invention is a fertilized oocyte or an embryonic stem cell into which Pablo-coding sequences have been introduced. Such host cells can then be used to create non-human transgenic animals in which exogenous Pablo sequences have been introduced into their genome or homologous recombinant animals in which endogenous Pablo sequences have been altered. Such animals are useful for studying the function and/or activity of a Pablo polypeptide and for identifying and/or evaluating modulators of Pablo activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous Pablo gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a Pablo-encoding nucleic acid into the male pronucleous of a fertilized oocyte, e.g., by microinjection, retroviral infection, and allowing the oocyte to develop in a pseudopregnant female foster animal. The Pablo sequence of SEQ ID NO:1 or portion thereof can be introduced as a transgene into the genome of a non-human animal. Alternatively, a nonhuman homologue of a Pablo gene, such as a mouse or rat Pablo gene, can be used as a transgene. Alternatively, a Pablo gene homologue, such as another Pablo family member, can be isolated based on hybridization to the Pablo family cDNA sequences of SEQ ID NO:1 (described further above) and used as a transgene.

Intronic sequences and polyadenylation signals can also be included in the transgene to increase the efficiency of expression of the transgene. A tissue-specific regulatory sequence(s) can be operably linked to a Pablo transgene to direct expression of a Pablo protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a Pablo transgene in its genome and/or expression of Pablo mRNA in tissues or cells of the animals. A transgenic founder animal can then be used to breed additional animals carrying the transgene. Moreover, transgenic animals carrying a transgene encoding a Pablo protein can further be bred to other transgenic animals carrying other transgenes.

To create a homologous recombinant animal, a vector is prepared which contains at least a portion of a Pablo gene into which a deletion, addition or substitution has been introduced to thereby alter, e.g., functionally disrupt, the Pablo gene. For example, a mouse Pablo gene can be used to construct a homologous recombination vector suitable for altering an endogenous Pablo gene in the mouse genome. In a preferred embodiment, the vector is designed such that, upon homologous recombination, the endogenous Pablo gene is functionally disrupted (i.e., no longer encodes a functional protein; also referred to as a "knock out" vector). Alternatively, the vector can be designed such that, upon homologous recombination, the endogenous Pablo gene is mutated or otherwise altered but still encodes a functional protein (e.g., the upstream regulatory region can be altered to thereby alter the expression of the endogenous Pablo protein). In the homologous recombination vector, the altered portion of the Pablo gene is flanked at its 5' and 3' ends by additional nucleic acid sequence of the Pablo gene to allow for homologous recombination to occur between the exogenous Pablo gene carried by the vector and an endogenous Pablo gene in an embryonic stem cell. The additional flanking Pablo nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Pablo gene has homologously recombined with the endogenous Pablo gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarci-* nomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) Nucl. Acids Res. 21:2025–2029; and Fukushige, S. and Sauer, B. (1992) Proc. Natl. Acad. Sci. USA 89:7905–7909) and the FLP recombinase-FRT target system (e.g., as described in Dang, D. T. and Perrimon, N. (1992) Dev. Genet. 13:367–375; and Fiering, S. et al. (1993) Proc. Natl. Acad. Sci. USA 90:8469–8473). Tetracycline-regulated inducible homologous recombination systems, such as described in PCT Publication No. WO 94/29442 and PCT Publication No. WO 96/01313, also can be used.

For example, in another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. Uses and Methods of the Invention

The nucleic acid molecules, proteins, protein homologues, and antibodies described herein can be used in one or more of the following methods: a) methods of treatment, e.g., up- or down-modulating apoptosis, preferably neural cell apoptosis; b) screening assays; c) predictive medicine (e.g., diagnostic assays, prognostic assays, monitoring clinical trials, or pharmacogenetics). The isolated nucleic acid molecules of the invention can be used, for example, to express Pablo protein (e.g., via a recombinant expression vector in a host cell in gene therapy applications), to detect Pablo mRNA (e.g., in a biological sample) or a genetic alteration in a Pablo gene, and to modulate Pablo activity, as described further below. The Pablo proteins can be used to treat disorders characterized by insufficient or excessive production of Pablo inhibitors. In addition, the Pablo proteins can be used to screen for naturally occurring Pablo binding proteins, to screen for drugs or compounds which modulate Pablo activity, as well as to treat disorders that would benefit from modulation of Pablo, e.g., characterized by insufficient or excessive production of Pablo protein or production of Pablo protein forms which have decreased or aberrant activity compared to Pablo wild type protein. Moreover, the anti-Pablo antibodies of the invention can be used to detect and isolate Pablo proteins, regulate the bioavailability of Pablo proteins, and modulate Pablo activity e.g., modulate apoptosis. In preferred embodiments the methods of the invention, e.g., detection, modulation of Pablo, etc. are performed in neural cells, e.g., cells of the central or peripheral nervous system.

A. Methods of Modulating Pablo:

The present invention provides for methods of modulating Pablo in a cell, e.g., for the purpose of identifying agents that modulate Pablo expression and/or activity, as well as both prophylactic and therapeutic methods of treating a subject at risk of (or susceptible to) a disorder or having a disorder associated with aberrant Pablo expression or activity or a disorder that would benefit from modulation of Pablo activity.

Yet another aspect of the invention pertains to methods of modulating Pablo expression and/or activity in a cell. The modulatory methods of the invention involve contacting the cell with an agent that modulates Pablo expression and/or activity such that Pablo expression and/or activity in the cell is modulated. The agent may act by modulating the activity of Pablo protein in the cell or by modulating transcription of the Pablo gene or translation of the Pablo mRNA.

Accordingly, in one embodiment, the agent inhibits Pablo activity. An inhibitory agent may function, for example, by directly inhibiting Pablo pro-apoptotic activity or by modulating a signaling pathway which negatively regulates Pablo. In another embodiment, the agent stimulates Pablo activity. A stimulatory agent may function, for example, by directly stimulating Pablo pro-apoptotic activity, or by modulating a signaling pathway that leads to stimulation of Pablo activity. Exemplary inhibitory agents include antisense Pablo nucleic acid molecules (e.g., to inhibit translation of Pablo mRNA), intracellular anti-Pablo antibodies (e.g., to inhibit the activity of Pablo protein), and dominant negative mutants of the Pablo protein. Other inhibitory agents that can be used to inhibit the activity of a Pablo protein are chemical compounds that inhibit Pablo-apoptotic activity. Such compounds can be identified using screening assays that select for such compounds, as described herein. Additionally or alternatively, compounds that inhibit Pablo-apoptotic activity can be designed using approaches known in the art.

According to another modulatory method of the invention, Pablo activity is stimulated in a cell by contacting the cell with a stimulatory agent. Examples of such stimulatory agents include active Pablo protein and nucleic acid molecules encoding Pablo that are introduced into the cell to increase Pablo activity in the cell. A preferred stimulatory agent is a nucleic acid molecule encoding a Pablo protein, wherein the nucleic acid molecule is introduced into the cell in a form suitable for expression of the active Pablo protein in the cell. To express a Pablo protein in a cell, typically a Pablo cDNA is first introduced into a recombinant expression vector using standard molecular biology techniques, as described herein. A Pablo cDNA can be obtained, for example, by amplification using the polymerase chain reaction (PCR) or by screening an appropriate cDNA library as described herein. Following isolation or amplification of Pablo cDNA, the DNA fragment is introduced into an expression vector and transfected into target cells by standard methods, as described herein. Other stimulatory agents that can be used to stimulate the activity and/or expression of a Pablo protein are chemical compounds that stimulate Pablo activity and/or expression in cells, such as compounds that enhance Pablo pro-apoptotic activity. Such compounds can be identified using screening assays that select for such compounds, as described in detail herein.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (i.e., cultured) in vitro with a modulatory agent of the invention to modulate Pablo activity in the cells.

For stimulatory or inhibitory agents that comprise nucleic acids (including recombinant expression vectors encoding Pablo protein, antisense RNA, intracellular antibodies or dominant negative inhibitors), the agents can be introduced into cells of the subject using methods known in the art for introducing nucleic acid (e.g., DNA) into cells in vivo. Examples of such methods encompass both non-viral and viral methods, including:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) *Gene Therapy* 2:38–49; San, H. et al. (1993) *Human Gene Therapy* 4:781–788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

There are a wide variety of pathological conditions for which Pablo modulating agents of the present invention can be used in treatment. In one embodiment, such agents can upmodulate apoptosis in a cell. In a further embodiment this method can be used to treat a subject suffering from a disorder which would benefit from the upmodulation of apoptosis. In a preferred embodiment, Pablo is modulated to enhance apoptosis of a neural cell, such as to promote the apoptosis in cancer cells of the nervous system. In another embodiment, is modulated to downmodulate apoptosis in a cell, preferably a neural cell, such as in the promotion of neural cell survival in Alzheimer's or amyotrophic lateral sclerosis (ALS) patients (Lee, M, 1999. J. of Neuropath & Exper. Neurology 58:459; Desjardins, P. and Ledoux, S. 1998. Neurosci. Letters. 244:69; Yosbihisa et al. 1998. Brain Research. 780:260). Other exemplary disorders for which modulation of Pablo can be used in treatment include other nervous system disorders. The term disorder is meant to include both normal conditions that would benefit from an alteration in Pablo activity and/or expression and various disease states.

1. Prophylactic Methods

In one aspect, the invention provides a method for preventing in a subject, a disease or condition that would benefit from modulation of Pablo activity and/or expression, e.g., a disorder associated with an aberrant Pablo expression or activity, by administering to the subject a Pablo polypeptide or an agent which modulates Pablo polypeptide expression or at least one Pablo activity. Subjects at risk for a disease which is caused or contributed to by aberrant Pablo expression or activity can be identified by, for example, any or a combination of diagnostic or prognostic assays as described herein. Administration of a prophylactic agent can occur prior to the manifestation of symptoms characteristic of Pablo aberrance, such that a disease or disorder is prevented or, alternatively, delayed in its progression. Depending on the type of Pablo aberrance or condition, for example, a Pablo polypeptide, Pablo agonist or Pablo antagonist agent can be used for treating the subject. The appropriate agent can be determined based on screening assays described herein.

2. Therapeutic Methods

Another aspect of the invention pertains to methods of modulating Pablo expression or activity for therapeutic purposes. Accordingly, in an exemplary embodiment, the modulatory method of the invention involves contacting a cell with a Pablo polypeptide or agent that modulates one or more of the activities of Pablo protein associated with the cell. An agent that modulates Pablo protein activity can be an agent as described herein, such as a nucleic acid or a protein, a naturally-occurring target molecule of a Pablo protein (e.g., a Pablo binding protein), a Pablo antibody, a Pablo agonist or antagonist, a peptidomimetic of a Pablo agonist or antagonist, or other small molecule. In one embodiment, the agent stimulates one or more Pablo activities. Examples of such stimulatory agents include active Pablo protein and a nucleic acid molecule encoding Pablo polypeptide that has been introduced into the cell. In another embodiment, the agent inhibits one or more Pablo activities. Examples of such inhibitory agents include, e.g., antisense Pablo nucleic acid molecules, anti-Pablo antibodies, and Pablo inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder that would benefit from modulation of a Pablo protein, e.g., a disorder which would benefit from up- or down-modulation of the immune response, or which is characterized by aberrant expression or activity of a Pablo protein or nucleic acid molecule. In one embodiment, the method involves administering an agent (e.g., an agent identified by a screening assay described herein), or combination of agents that modulates (e.g., upregulates or downregulates) Pablo expression or activity. In another embodiment, the method involves administering a Pablo protein or nucleic acid molecule as therapy to compensate for reduced or aberrant Pablo expression or activity.

Stimulation of Pablo activity is desirable in situations in which Pablo is abnormally downregulated and/or in which increased Pablo activity is likely to have a beneficial effect, e.g., when it is desirable to increase apoptosis in a cell. Likewise, inhibition of Pablo activity is desirable in situations in which Pablo is abnormally upregulated and/or in which decreased Pablo activity is likely to have a beneficial effect, e.g., when it is desirable to decrease apoptosis in a cell. Exemplary situations in which Pablo modulation will be desirable are in the treatment of Pablo associated disorders.

B. Screening Assays:

The invention provides a method (also referred to herein as a "screening assay") for identifying modulators, i.e., candidate or test compounds or agents (e.g., peptides, peptidomimetics, small molecules or other drugs) which bind to Pablo proteins, have a stimulatory or inhibitory effect on, for example, Pablo expression or Pablo activity.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladnersupra.).

In many drug screening programs which test libraries of modulating agents and natural extracts, high throughput assays are desirable in order to maximize the number of modulating agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test modulating agent. Moreover, the effects of cellular toxicity and/or bioavailability of the test modulating agent can be generally ignored in the in vitro system, the assay instead being focused primarily on the effect of the drug on the molecular target as may be manifest in an alteration of binding affinity with upstream or downstream elements.

In one embodiment, the invention provides assays for screening candidate or test compounds which bind to or modulate the activity of a Pablo protein or polypeptide or biologically active portion thereof, e.g., modulate the ability of Pablo polypeptide to interact with Bcl-xL.

Assays can be used to screen for modulating agents, including Pablo homologs, which are either agonists or antagonists of the normal cellular function of the subject Pablo polypeptides. For example, the invention provides a method in which an indicator composition is provided which has a Pablo protein having a Pablo activity. The indicator composition can be contacted with a test compound. The effect of the test compound on Pablo activity, as measured by a change in the indicator composition, can then be determined to thereby identify a compound that modulates the activity of a Pablo protein. A statistically significant change, such as a decrease or increase, in the level of Pablo activity in the presence of the test compound (relative to what is detected in the absence of the test compound) is indicative of the test compound being a Pablo modulating agent. The indicator composition can be, for example, a cell or a cell extract. In one embodiment, Pablo activity is assessed as described in the appended Examples.

In an exemplary screening assay of the present invention, the modulating agent of interest is contacted with interactor proteins which may function upstream (including both activators and repressors of its activity) or to proteins which may function downstream of the Pablo protein, whether they are positively or negatively regulated by it. To the mixture of the modulating agent and the upstream or downstream element is then added a composition containing a Pablo protein. Detection and quantification of the interaction of Pablo with it's upstream or downstream elements provide a means for determining a modulating agent's efficacy at inhibiting (or potentiating) complex formation between Pablo and the Pablo binding elements.

The efficacy of the modulating agent can be assessed by generating dose response curves from data obtained using various concentrations of the test modulating agent. Moreover, a control assay can also be performed to provide a baseline for comparison. In the control assay, isolated and purified Pablo protein is added to a composition containing the Pablo-binding element, and the formation of a complex is quantitated in the absence of the test modulating agent.

In yet another embodiment, an assay of the present invention is a cell-free assay in which a Pablo protein or biologically active portion thereof is contacted with a test compound and the ability of the test compound to bind to the Pablo protein or biologically active portion thereof is determined. Binding of the test compound to the Pablo protein can be determined either directly or indirectly as described above. In a preferred embodiment, the assay includes contacting the Pablo protein or biologically active portion thereof with a known compound which binds Pablo to form an assay mixture, contacting the assay mixture with a test compound, and determining the ability of the test compound to interact with a Pablo protein, wherein determining the ability of the test compound to interact with a Pablo protein comprises determining the ability of the test compound to preferentially bind to Pablo polypeptide or biologically active portion thereof as compared to the known compound.

In another embodiment, the assay is a cell-free assay in which a Pablo protein or biologically active portion thereof is contacted with a test compound and the ability of the test compound to modulate (e.g., stimulate or inhibit) the activity of the Pablo protein or biologically active portion thereof is determined. The Pablo protein can be provided as a lysate of cells that express Pablo, as a purified or semipurified polypeptide, or as a recombinantly expressed polypeptide. In one embodiment, a cell-free assay system further comprises a cell extract or isolated components of a cell, such as mitochondria. Such cellular components can be isolated using techniques which are known in the art. Preferably, a cell free assay system further comprises at least one target molecule with which Pablo interacts, and the ability of the test compound to modulate the interaction of the Pablo with the target molecule(s) is monitored to thereby identify the test compound as a modulator of Pablo, e.g., Bcl-xL activity. Determining the ability of the test compound to modulate the activity of a Pablo protein can be accomplished, for example, by determining the ability of the Pablo protein to bind to a Pablo target molecule, e.g., Bcl-xL by one of the methods described above for determining direct binding. Determining the ability of the Pablo protein to bind to a Pablo target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting a Pablo protein or biologically active portion thereof with a known compound which binds the Pablo protein to form an assay mixture, contacting the assay mixture with a test compound, and determining the ability of the test compound to interact with the Pablo protein, wherein determining the ability of the test compound to interact with the Pablo protein comprises determining the ability of the Pablo protein to preferentially bind to or modulate the activity of a Pablo target molecule.

The cell-free assays of the present invention are amenable to use of both soluble and/or membrane-bound forms of proteins (e.g., Pablo proteins or receptors having intracellular domains to which Pablo binds). In the case of cell-free assays in which a membrane-bound form a protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

A Pablo target molecule can be a protein or a DNA sequence. Suitable assays are known in the art that allow for the detection of protein-protein interactions (e.g., immunoprecipitations, two-hybrid assays and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of Pablo with a target molecule(s).

Determining the ability of the Pablo protein to bind to or interact with a ligand of a Pablo molecule can be accomplished, e.g., by direct binding. In a direct binding assay, the Pablo protein could be coupled with a radioisotope or enzymatic label such that binding of the Pablo protein to a Pablo target molecule can be determined by detecting the labeled Pablo protein in a complex. For example, Pablo molecules, e.g., Pablo proteins, can be labeled with $^{125}$I, $^{35}$S, $^{14}$C, or $^3$H, either directly or indirectly, and the radioisotope detected by direct counting of radioemmission or by scintillation counting. Alternatively, Pablo molecules can be enzymatically labeled with, for example, horseradish peroxidase, alkaline phosphatase, or luciferase, and the enzymatic label detected by determination of conversion of an appropriate substrate to product.

Typically, it will be desirable to immobilize either Pablo or its binding protein to facilitate separation of complexes from uncomplexed forms of one or both of the proteins, as well as to accommodate automation of the assay. Binding of Pablo to an upstream or downstream binding element, in the presence and absence of a candidate agent, can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase/Pablo (GST/Pablo) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test modulating agent, and the mixture incubated under conditions conducive to complex formation, e.g., at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of Pablo-binding protein found in the bead fraction quantitated from the gel using standard electrophoretic techniques.

Other techniques for immobilizing proteins on matrices are also available for use in the subject assay. For instance, either Pablo or its cognate binding protein can be immobilized utilizing conjugation of biotin and streptavidin. For instance, biotinylated Pablo molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Pablo but which do not interfere with binding of upstream or downstream elements can be derivatized to the wells of the plate, and Pablo trapped in the wells by antibody conjugation. As above, preparations of a Pablo-binding protein and a test modulating agent are incubated in the Pablo-presenting wells of the plate, and the amount of complex trapped in the well can be quantitated. Exemplary methods for detecting such complexes, in addition to those described above for the GST-immobilized complexes, include immunodetection of complexes using antibodies reactive with the Pablo binding element, or which are reactive with Pablo protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the Pablo-BP. To illustrate, the Pablo-BP can be chemically cross-linked or genetically fused with horseradish peroxidase, and the amount of protein trapped in the complex can be assessed with a chromogenic substrate of the enzyme, e.g. 3,3'-diaminobenzadine terahydrochloride or 4-chloro-1-napthol. Likewise, a fusion protein comprising the protein and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-Pablo antibodies, can be used. Alternatively, the protein to be detected in the complex can be "epitope tagged" in the form of a fusion protein which includes, in addition to the Pablo sequence, a second protein for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

It is also within the scope of this invention to determine the ability of a compound to modulate the interaction between Pablo and its target molecule, without :the labeling of any of the interactants. For example, a microphysiometer can be used to detect the interaction of Pablo with its target molecule without the labeling of either Pablo or the target molecule. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In addition to cell-free assays, the readily available source of Pablo proteins provided by the present invention also facilitates the generation of cell-based assays for identifying small molecule agonists/antagonists and the like. For example, cells can be caused to express or overexpress a recombinant Pablo protein in the presence and absence of a test modulating agent of interest, with the assay scoring for modulation in Pablo responses by the target cell mediated by the test agent. For example, as with the cell-free assays, modulating agents which produce a statistically significant change in Pablo-dependent responses (either an increase or decrease) can be identified.

Recombinant expression vectors that can be used for expression of Pablo are known in the art (see discussions above). In one embodiment, within the expression vector the Pablo-coding sequences are operatively linked to regulatory sequences that allow for constitutive or inducible expression of Pablo in the indicator cell(s). Use of a recombinant expression vector that allows for constitutive or inducible expression of Pablo in a cell is preferred for identification of compounds that enhance or inhibit the activity of Pablo. In an alternative embodiment, within the expression vector the Pablo coding sequences are operatively linked to regulatory sequences of the endogenous Pablo gene (i.e., the promoter regulatory region derived from the endogenous gene). Use of a recombinant expression vector in which Pablo expression is controlled by the endogenous regulatory sequences is preferred for identification of compounds that enhance or inhibit the transcriptional expression of Pablo. In one embodiment, an assay is a cell-based assay comprising contacting a cell expressing a Pablo target molecule (e.g., Bcl-xL or another Pablo intracellular interacting molecule) with a test compound and determining the ability of the test compound to modulate (e.g. stimulate or inhibit) the activity of the Pablo target molecule. Determining the ability of the test compound to modulate the activity of a Pablo target molecule can be accomplished, for example, by determining the ability of the Pablo protein to bind to or interact with the Pablo target molecule or its ligand.

In an illustrative embodiment, the expression or activity of a Pablo is modulated in cells and the effects of modulating agents of interest on the readout of interest (such as apoptosis) are measured. In one embodiment, the regulatory regions of genes whose transcription is altered by a modulation in Pablo expression or activity, e.g., the 5' flanking promoter and enhancer regions, are operatively linked to a marker (such as luciferase) which encodes a gene product that can be readily detected.

In another embodiment, modulators of Pablo expression are identified in a method wherein a cell is contacted with a candidate compound and the expression of Pablo mRNA or protein in the cell is determined. The level of expression of Pablo mRNA or protein in the presence of the candidate compound is compared to the level of expression of Pablo mRNA or protein in the absence of the candidate compound. The candidate compound can then be identified as a modulator of Pablo expression based on this comparison. For example, when expression of Pablo mRNA or protein is greater (e.g., statistically significantly greater) in the presence of the candidate compound than in its absence, the candidate compound is identified as a stimulator of Pablo mRNA or protein expression. Alternatively, when expression of Pablo mRNA or protein is less (e.g., statistically significantly less) in the presence of the candidate compound than in its absence, the candidate compound is identified as an inhibitor of Pablo mRNA or protein expression. The level of Pablo mRNA or protein expression in the cells can be determined by methods described herein for detecting Pablo mRNA or protein.

In a preferred embodiment, determining the ability of the Pablo protein to bind to or interact with a Pablo target molecule can be accomplished by measuring a read out of the activity of Pablo or of the target molecule. For example, the activity of Pablo or a target molecule can be determined by detecting induction of a cellular second messenger of the target (e.g., a second messenger modulated by Bcl-xL), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response, e.g., apoptosis. For example, determining the ability of the Pablo protein to bind to or interact with a Pablo target molecule can be accomplished, for example, by measuring the ability of a compound to modulate apoptosis, preferably in a neural cell. The hallmark of apoptosis is degradation of DNA. Early in the process, this degradation occurs in internucleosomal DNA linker regions. The DNA cleavage may yield double-stranded and single-stranded DNA breaks. Apoptosis can be measured in cells using standard techniques. For example, degradation of genomic DNA of a population of cells can be analyzed by agarose gel electrophoresis, or DNA fragmentation assays based on 3H-thymidine or 5-Bromo-2'-deoxy-uridine can be used.

To analyze apoptosis in individual cells, apoptotic cells may be recognized microscopically because of the characteristic appearance of nuclear chromatin condensation and fragmentation. Apoptosis can be measured in individual cells, for example, using Hoechst stain and looking for cells with pyknotic nuclei as described in the appended Examples. Alternatively, double and single-stranded DNA breaks can be detected by labeling the free 3'-OH termini with modified nucleotides (e.g., biotin-dUTP, DIG-dUTP, fluorescein-dUTP) in an enzymatic reaction. Terminal deoxynucleotidyl transferase (TdT) catalyzes the template independent polymerization of deoxyribonucleotides to the 3' end of the DNA. This method is referred to as TUNEL (TdT-mediated dUTP-X nick end labeling). Alternatively, free 3'OH groups may be labeled using DNA polymerases by nick translation. tunnel staining can be used to identify cells with double stranded DNA breaks. Labeled free 3'OH groups that have incorporated labeled dUTP can be visualized by flow cytometry and/or fluorescence microscopy. Reagents for performing these assays are available e.g., from Roche Molecular Biochemicals USA (In situ cell death detection kit). In addition, annexin (e.g., Annexin-V-Alexa™ 568 commercially available from Roch molecular Biochemicals USA) can be used for this purpose. One of the early plasma membrane changes associated with cells undergoing apoptosis is the translocation of phosphatidylserine from the inner leaflet of the plasma membrane to the outer layer, thereby exposing phosphatidylserine at the surface of the cell. Annexin-V is a phospholipid binding protein which binds to phosphatidyl serine and can be used as a probe for phosphatidylserine on cell surfaces. Annexin-V can be used in combination with a DNA stain (e.g., BOBO™-1) to differentiate apoptotic cells from necrotic cells.

In yet another aspect of the invention Pablo proteins or portions thereof can be used as "bait proteins" in a two-hybrid assay or three-hybrid assay (see, e.g., U.S. Pat. No. 5,283,317; Zervos et al. (1993) $Cell$ 72:223–232; Madura et al. (1993) $J. Biol. Chem.$ 268:12046–12054; Bartel et al. (1993) $Biotechniques$ 14:920–924; Iwabuchi et al. (1993) $Oncogene$ 8:1693–1696; and Brent WO94/10300), to identify other proteins, which bind to or interact with Pablo ("Pablo-binding proteins" or "Pablo-bp") and are involved in Pablo activity. One such binding protein in Bcl-xL. Such Pablo-binding proteins are also likely to be involved in the propagation of signals by the Pablo proteins or Pablo targets as, for example, downstream elements of a Pablo-mediated signaling pathway. Alternatively, such Pablo-binding proteins may be Pablo inhibitors.

The two-hybrid system is based on the modular nature of most transcription factors, which consist of separable DNA-binding and activation domains. Briefly, the assay utilizes two different DNA constructs. In one construct, the gene that codes for a Pablo protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Pablo-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Pablo protein.

The present invention also provides a kit comprising a two-hybrid system having (1) a first hybrid protein comprising Pablo and a transcriptional activation domain (2) a second hybrid protein comprising a Bcl-xL polypeptide and a DNA-binding domain, a host cell, and an instruction manual. Alternatively, the Pablo polypeptide may be fused to the DNA-binding domain and the Bcl-xL polypeptide fused to the activation domains. Such kits may optionally include a panel of agents for testing for the capacity to alter intermolecular binding between the first and second hybrid proteins.

This invention further pertains to novel agents identified by the above-described screening assays. Accordingly, it is within the scope of this invention to further use an agent identified as described herein in an appropriate animal model. For example, an agent identified as described herein (e.g., a Pablo modulating agent, an antisense Pablo nucleic acid molecule, a Pablo-specific antibody, or a Pablo-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

C. Methods of Rational Drug Design

Pablo and Pablo binding polypeptides, e.g., Bcl-xL polypeptides, especially those portions which form direct contacts in Pablo/Bcl-xL heterodimers, can be used for rational drug design of candidate Pablo or Bcl-xL-modulating agents (e.g., antineoplastics and down modulators of apoptosis). The identification of Pablo as a binding partner for Bcl-xL as provided herein permits production of substantially pure Pablo/Bcl-xL polypeptide complexes and computational models which can be used for protein X-ray crystallography or other structure analysis methods, such as the DOCK program (Kuntz et al (1982) J. Mol. Biol. 161: 269; Kuntz ID (1992) Science 257: 1078) and variants thereof Potential therapeutic drugs may be designed rationally on the basis of structural information thus provided. In one embodiment, such drugs are designed to prevent or enhance formation of a Pablo polypeptide: Bcl-xL polypeptide complex. Thus, the present invention may be used to design drugs, including drugs with a capacity to inhibit or promote binding of Pablo to Bcl-xL.

D. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

E. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Pablo protein and/or nucleic acid expression as well as Pablo activity, in the context of a biological sample (e.g., blood, serum, cells, tissue (preferably neural cells or tissue)) to thereby determine whether an individual is afflicted with a disease or disorder, or is at risk of developing a disorder, associated with aberrant Pablo expression or activity. The invention also provides for prognostic (or predictive) assays for determining whether an individual is at risk of developing a disorder associated with Pablo protein, nucleic acid expression or activity. For example, mutations in a Pablo gene can be assayed in a biological sample. Such assays can be used for prognostic or predictive purpose to thereby prophylactically treat an individual prior to the onset of a disorder characterized by or associated with Pablo protein, nucleic acid expression or activity.

Another aspect of the invention pertains to monitoring the influence of agents (e.g., drugs, compounds) on the expression or activity of Pablo in clinical trials.

These and other agents are described in further detail in the following sections.

1. Diagnostic Assays

An exemplary method for detecting the presence or absence of Pablo protein or nucleic acid in a biological sample involves obtaining a biological sample from a test subject and contacting the biological sample with a compound or an agent capable of detecting Pablo protein or nucleic acid (e.g., mRNA, genomic DNA) that encodes Pablo protein such that the presence of Pablo protein or nucleic acid is detected in the biological sample. A preferred agent for detecting Pablo mRNA or genomic DNA is a labeled nucleic acid probe capable of hybridizing to Pablo mRNA or genomic DNA. The nucleic acid probe can be, for example, a Pablo nucleic acid, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to Pablo mRNA or genomic DNA. Other suitable probes for use in the diagnostic assays of the invention are described herein.

A preferred agent for detecting Pablo protein is an antibody capable of binding to Pablo protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells (preferably neural cells or tissue) and fluids present within a subject. That is, the detection method of the invention can be used to detect Pablo mRNA, protein, or genomic DNA in a biological sample in vitro as well as in vivo. For example, in vitro techniques for detection of Pablo mRNA include Northern hybridizations and in situ hybridizations. In vitro techniques for detection of Pablo protein include enzyme linked immunosorbent assays (ELISAs), Western blots, immunoprecipitation and immunofluorescence. In vitro techniques for detection of Pablo genomic DNA include Southern hybridizations. Furthermore, in vivo techniques for detection of Pablo protein include introducing into a subject a labeled anti-Pablo antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Pablo protein, mRNA, or genomic DNA, such that the presence of Pablo protein, mRNA or genomic DNA is detected in the biological sample, and comparing the presence of Pablo protein, mRNA or genomic DNA in the control sample with the presence of Pablo protein, mRNA or genomic DNA in the test sample.

The invention also encompasses kits for detecting the presence of Pablo in a biological sample. For example, the kit can comprise a labeled compound or agent capable of detecting Pablo protein or mRNA in a biological sample; means for determining the amount of Pablo in the sample; and means for comparing the amount of Pablo in the sample with a standard. The compound or agent can be packaged in a suitable container. The kit can further comprise instructions for using the kit to detect Pablo protein or nucleic acid.

2. Prognostic Assays

The diagnostic methods described herein can furthermore be utilized to identify subjects having or at risk of developing a disease or disorder associated with aberrant Pablo expression or activity. For example, the assays described herein, such as the preceding diagnostic assays or the following assays, can be utilized to identify a subject having or at risk of developing a disorder associated with Pablo protein, nucleic acid expression or activity. Thus, the present invention provides a method for identifying a disease or disorder associated with aberrant Pablo expression or activity in which a test sample is obtained from a subject and Pablo protein or nucleic acid (e.g., mRNA, genomic DNA) is detected, wherein the presence of Pablo protein or nucleic acid is diagnostic for a subject having or at risk of developing a disease or disorder associated with aberrant Pablo expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Pablo expression or activity. Thus, the present invention provides methods for determining whether a subject can be effectively treated with an agent for a disorder associated with aberrant Pablo expression or activity in which a test sample is obtained and Pablo protein or nucleic acid expression or activity is detected (e.g., wherein the abundance of Pablo protein or nucleic acid expression or activity is diagnostic for a subject that can be administered the agent to treat a disorder associated with aberrant Pablo expression or activity).

The methods of the invention can also be used to detect genetic alterations in a Pablo gene, thereby determining if a subject with the altered gene is at risk for a disorder associated with the Pablo gene. In preferred embodiments, the methods include detecting, in a sample of cells from the subject, the presence or absence of a genetic alteration characterized by at least one of an alteration affecting the integrity of a gene encoding a Pablo-protein, or the misexpression of the Pablo gene. For example, such genetic alterations can be detected by ascertaining the existence of at least one of 1) a deletion of one or more nucleotides from a Pablo gene; 2) an addition of one or more nucleotides to a Pablo gene; 3) a substitution of one or more nucleotides of a Pablo gene, 4) a chromosomal rearrangement of a Pablo gene; 5) an alteration in the level of a messenger RNA transcript of a Pablo gene, 6) aberrant modification of a Pablo gene, such as of the methylation pattern of the genomic DNA, 7) the presence of a non-wild type splicing pattern of a messenger RNA transcript of a Pablo gene, 8) a non-wild type level of a Pablo protein, 9) allelic loss of a Pablo gene, and 10) inappropriate post-translational modification of a Pablo protein. As described herein, there are a large number of assay techniques known in the art which can be used for detecting alterations in a Pablo gene. A preferred biological sample is a tissue or serum sample isolated by conventional means from a subject, e.g., a neural tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the Pablo gene (see Abravaya et al. (1995) *Nucleic Acids Res*. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a Pablo gene under conditions such that hybridization and amplification of the Pablo gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Pablo gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Pablo can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2:753–759). For example, genetic mutations in Pablo can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Pablo gene and detect mutations by comparing the sequence of the sample Pablo with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr*. 36:127–162; and Griffin et al. (1993) *Appl. Biochem. Biotechnol*. 38:147–159).

Other methods for detecting mutations in the Pablo gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type Pablo sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol*. 217:286–295. In a preferred embodiment, the control DNA or RNA can be labeled for detection. In still another embodiment, the mismatch cleavage reaction employs one or more proteins that recognize mismatched base pairs in double-stranded DNA (so called "DNA mismatch repair" enzymes) in defined systems for detecting and mapping point mutations in Pablo obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Pablo sequence, e.g., a wild-type Pablo sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Pablo genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat Res* 285:125–144; and Hayashi (1992) *Genet Anal Tech Appl* 9:73–79). Single-stranded DNA fragments of sample and control Pablo nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Pablo gene.

Furthermore, any cell type or tissue in which Pablo is expressed may be utilized in the prognostic assays described herein.

VI. Administration of Pablo Modulating Agents

Pablo modulating agents of the invention are administered to subjects in a biologically compatible form suitable for pharmaceutical administration in vivo to either enhance or suppress T cell mediated immune response. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a Pablo modulating agent may vary according to factors such as the disease state, age, sex, and weight of the individual, and the ability of peptide to elicit a desired response in the individual. Dosage regima may be adjusted to provide the optimum therapeutic response. For example, several divided doses may be administered daily or the dose may be proportionally reduced as indicated by the exigencies of the therapeutic situation.

The therapeutic or pharmaceutical compositions of the present invention can be administered by any suitable route known in the art including for example intravenous, subcutaneous, intramuscular, transdermal, intrathecal or intracerebral or administration to cells in ex vivo treatment protocols. Administration can be either rapid as by injection or over a period of time as by slow infusion or administration of slow release formulation. For treating tissues in the central nervous system, administration can be by injection or infusion into the cerebrospinal fluid (CSF). When it is intended that a Pablo polypeptide be administered to cells in the central nervous system, administration can be with one or more agents capable of promoting penetration of Pablo polypeptide across the blood-brain barrier.

Pablo can also be linked or conjugated with agents that provide desirable pharmaceutical or pharmacodynamic properties. For example, Pablo can be coupled to any substance known in the art to promote penetration or transport across the blood-brain barrier such as an antibody to the transferrin receptor, and administered by intravenous injection. (See for example, Friden et al., Science 259: 373–377, 1993 which is incorporated by reference). Furthermore, Pablo can be stably linked to a polymer such as polyethylene glycol to obtain desirable properties of solubility, stability, half-life and other pharmaceutically advantageous properties. (See for example Davis et al. Enzyme Eng 4: 169–73, 1978; Burnham, Am J Hosp Pharm 51: 210–218, 1994 which are incorporated by reference).

Furthermore, the Pablo polypeptide can be in a composition which aids in delivery into the cytosol of a cell. For example, the peptide may be conjugated with a carrier moiety such as a liposome that is capable of delivering the peptide into the cytosol of a cell. Such methods are well known in the art (for example see Amselem et al., Chem Phys Lipids 64: 219–237, 1993 which is incorporated by reference). Alternatively, the Pablo polypeptide can be modified to include specific transit peptides or fused to such transit peptides which are capable of delivering the Pablo polypeptide into a cell. In addition, the polypeptide can be delivered directly into a cell by microinjection.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. Pablo can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used.

It is also provided that certain formulations containing the Pablo polypeptide or fragment thereof are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of this invention, a Pablo polypeptide may be therapeutically administered by implanting into patients vectors or cells capable of producing a biologically-active form of Pablo or a precursor of Pablo, i.e. a molecule that can be readily converted to a biological-active form of Pablo by the body.

In one approach cells that secrete Pablo may be encapsulated into semipermeable membranes for implantation into a patient. The cells can be cells that normally express Pablo or a precursor thereof or the cells can be transformed to express Pablo or a biologically active fragment thereof or a precursor thereof. It is preferred that the cell be of human origin and that the Pablo polypeptide be human Pablo when the patient is human. However, the formulations and methods herein can be used for veterinary as well as human applications and the term "patient" or "subject" as used herein is intended to include human and veterinary patients.

Monitoring the influence of agents (e.g., drugs or compounds) on the expression or activity of a Pablo protein can be applied not only in basic drug screening, but also in clinical trials. For example, the effectiveness of an agent determined by a screening assay as described herein to increase Pablo gene expression, protein levels, or upregulate Pablo activity, can be monitored in clinical trials of subjects exhibiting decreased Pablo gene expression, protein levels, or downregulated Pablo activity. Alternatively, the effectiveness of an agent determined by a screening assay to decrease Pablo gene expression, protein levels, or downregulate Pablo activity, can be monitored in clinical trials of subjects exhibiting increased Pablo gene expression, protein levels, or upregulated Pablo activity. In such clinical trials, the expression or activity of a Pablo gene, and preferably, other genes that have been implicated in a disorder can be used as a "read out" or markers of the phenotype of a particular cell.

For example, and not by way of limitation, genes, including Pablo, that are modulated in cells by treatment with an agent (e.g., compound, drug or small molecule) which modulates Pablo activity (e.g., identified in a screening assay as described herein) can be identified. Thus, to study the effect of agents on a Pablo associated disorder, for example, in a clinical trial, cells can be isolated and RNA prepared and analyzed for the levels of expression of Pablo and other genes implicated in the Pablo associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Pablo or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Pablo protein, mRNA, or genomic DNA in the pre-administration sample; (iii) obtaining one or more post-administration samples from the subject; (iv) detecting the level of expression or activity of the Pablo protein, mRNA, or genomic DNA in the post-administration samples; (v) comparing the level of expression or activity of the Pablo protein, mRNA, or genomic DNA in the pre-administration sample with the Pablo protein, mRNA, or genomic DNA in the post administration sample or samples; and (vi) altering the administration of the agent to the subject accordingly. For example, increased administration of the agent may be desirable to increase the expression or activity of Pablo to higher levels than detected, i.e., to increase the effectiveness of the agent. Alternatively, decreased administration of the agent may be desirable to decrease expression or activity of Pablo to lower levels than detected, i.e. to decrease the effectiveness of the agent. According to such an embodiment, Pablo expression or activity may be used as an indicator of the effectiveness of an agent, even in the absence of an observable phenotypic response.

In a preferred embodiment, the ability of a Pablo modulating agent to modulate apoptosis in a neural cell of a subject that would benefit from modulation of the expression and/or activity of Pablo can be measured by detecting an improvement in the condition of the patient after the administration of the agent. Such improvement can be readily measured by one of ordinary skill in the art using indicators appropriate for the specific condition of the patient. Monitoring the response of the patient by measuring changes in the condition of the patient is preferred in situations were the collection of biopsy materials would pose an increased risk and/or detriment to the patient.

It is likely that the level of Pablo may be altered in a variety of conditions and that quantification of Pablo levels would provide clinically useful information. Furthermore, because it has been demonstrated herein that increased levels of Pablo expressed by a cell can shift the cell death regulatory mechanism of that cell to decrease viability, it is believed that measurement of the level of Pablo in a cell or cells such as in a group of cells, tissue or neoplasia, like will provide useful information regarding apoptotic state of that cell or cells. In addition, because, Pablo interacts with Bcl-xL, it can also be desirable to determine the cellular levels of these Pablo-interacting Bcl-xL family members.

Furthermore, in the treatment of disease conditions, compositions containing Pablo can be administered exogenously and it would likely be desirable to achieve certain target levels of Pablo polypeptide in sera, in any desired tissue compartment or in the affected tissue. It would, therefore, be advantageous to be able to monitor the levels of Pablo polypeptide in a patient or in a biological sample including a tissue biopsy sample obtained form a patient and, in some cases, also monitoring the levels of Pablo and, in some circumstances, also monitoring levels of BCL-xL. Accordingly, the present invention also provides methods for detecting the presence of Pablo in a sample from a patient.

VII. Kits of the Invention

Another aspect of the invention pertains to kits for carrying out the screening assays, modulatory methods or diagnostic assays of the invention. For example, a kit for carrying out a screening assay of the invention can include a cell comprising a Pablo polypeptide, means for determining Pablo polypeptide activity and instructions for using the kit to identify modulators of Pablo activity. In another embodiment, a kit for carrying out a screening assay of the invention can include an composition comprising a Pablo polypeptide, means for determining Pablo activity and instructions for using the kit to identify modulators of Pablo activity.

In another embodiment, the invention provides a kit for carrying out a modulatory method of the invention. The kit can include, for example, a modulatory agent of the invention (e.g., a Pablo inhibitory or stimulatory agent) in a suitable carrier and packaged in a suitable container with instructions for use of the modulator to modulate Pablo activity.

Another aspect of the invention pertains to a kit for diagnosing a disorder associated with aberrant Pablo expression and/or activity in a subject. The kit can include a reagent for determining expression of Pablo (e.g., a nucleic acid probe(s) for detecting Pablo mRNA or one or more antibodies for detection of Pablo proteins), a control to which the results of the subject are compared, and instructions for using the kit for diagnostic purposes.

The contents of all cited references, including literature references, issued patents, published patent applications as cited throughout this application (including the background) are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The present invention is further illustrated by the following examples which should not be construed as limiting in any way.

Example 1

Identification of Pablo as a Bcl-xL Binding Protein

Bcl-xL was expressed as a fusion protein in the binding domain portion of the GAL4 protein in the pAS2-1 vector. The human brain library (Adult human brain Matchmaker cDNA From Clontech; cat# HL4004AH, lot# 52008) was expressed in the form of fusions to the activation domain portion of the GALA protein in the pACT II vector. Functional interaction of Bcl-xL with a library protein drove the expression of the reporter gene activity. The reporter phenotypes we utilized were histidine prototrophy and beta-galactosidase activity.

The Bcl-xL used as bait was the human cDNA from the start codon to nucleotide 658 (SEQ ID NO: 3). This corresponds to amino acids 1–211 (SEQ ID NO: 4). In other words, the last 22 amino acids, which are believed to be a transmembrane region, were deleted.

Library transformation and screening was performed as per Clontech instructions. Three of the clones which were positive for growth on his- plates and positive for beta-galactosidase activity encoded portions of a previously identified human brain EST: KIAA0269, referred to herein as Pablo-Pro-Apoptotic Bcl-xL binding protein. As described in more detail below, two of these clones coded for approximately the last 130 amino acids (amino acids 429–559) of Pablo were found to be sufficient for binding to Bcl-xL.

A clone coding for the fill open reading frame of Pablo was generated using primers designed against sequences around the ATG and stop codon reported in the GenBank submission for KIAA0269.

The clone identified in this assay was sequenced and confirmed to match the sequence in the KIAA0269 GenBank submission (Accession number D87459). KIAA0269 encodes a polypeptide originally predicted by Nagase et al. (DNA Research (1996) 3:321–324) and referred to in that reference as KIAA0269. Nagase and colleagues originally identified the KIAA0269 expressed sequence tag (EST) fragment as part of a project aimed at sequencing human cDNA clones.

Pablo is a novel member of the WASP (Wiskott-Aldrich Syndrome Protein) family of proteins (Derry et al., 1994. Cell. 78:635; Ramesh et al., 1999. Trends Cell Biol. 9:15). The WASP family are actin binding proteins which are believed to be involved in rearrangement of the microfilament component of the cellular cytoskeleton. There is evidence of tissue specific expression of various WASP family members. In keeping with KIAA's expression pattern, the protein is most homologous to N-WASP (a neuron-specific WASP family member) (Miki et al., 1996. EMBO 15:5326). A recent report by Bear et al., (1998. J. Cell Biol. 142:1325) demonstrates that Pablo is the human homologue of the Dictyostelium gene SCAR. In another report, Machesky et al. (1998. Curr. Biol. 8:1347), report that Scar1 (Pablo) regulates the actin cytoskeleton through an interaction with actin associated proteins Arp2/3 (Machesky et al., 1997. Biochem. J. 328:105; Mullins et al., 1998 Proc. Natl. Acad. Sci. USA 95:6181).

Northern blots indicated that Pablo is expressed predominantly in the brain, but is also expressed at lower levels in the testis and ovary.

Example 2

Pablo Over-Expression is Toxic to Cerebellar Granular Neurons

Cerebellar Granular Neurons (CGNs) were transiently transfected with a Pablo-eGFP-C2 construct (the eGFP vector is commercially available from Clontech; Palo Alto, Calif.) using the calcium phosphate ProFectin® Mammalian Transfection System (Promega Corporation, Madison, Wis.) according to the manufacturer's instructions. Images were made of transfected CGNs 8 hours post-transfection. Each image was an optical section through the neuron taken with a confocal microscope. The fluorescent signal was detected from the Pablo-eGFP fusion construct. The images showed that at this 8 hour time point, the Pablo protein is localized primarily to the plasma membrane. The findings were. representative of over 30 CGN examined. There is nothing in the secondary structure of this protein to suggest that it has any transmembrane regions and thus is an integral membrane protein. Rather, as stated above, it shares homology with families of proteins that are associated with the actin component of the cytoskeleton. Therefore, Pablo is associated with the plasma membrane, not in it.

In another panel of images made 24 hours post-transfection with the Pablo-eGFP construct, the localization pattern was different from that obtained at. At 24 hours the Pablo protein was not restricted to a plasma membrane locale, but rather appeared diffuse throughout the cytosol. Also, while fluorescence is diffuse, there does not appear to be any nuclear localization. The findings were representative of over 30 neurons examined.

At approximately 36 hours post-transfection, cell bodies appeared irregular in shape and the neurites were fragmented. Pablo distribution continued to be diffuse throughout the cell, but excluded from the nucleus. By 48 hours all eGFP positive CGNs were fragmented debris. In each culture, at each time point, the untransfected neurons remained healthy.

Example 3

Pablo Overexpression is Toxic in Primary Rat Hippocampal Neurons

Primary rat hippocampal cultures (10 days in culture) on glass coverslips were transfected using the calcium phosphate ProFectin® Mammalian Transfection System (Promega Corporation, Madison, Wis.). Approximately 30 hours post-transfection, cultures were fixed in 4% paraformaldehyde, Hoechst stained, and mounted on glass slides. eGFP positive cells were scored for apoptotic nuclei. Thirty percent of the hippocampal neurons transfected with the eGFP empty vector showed apoptotic nuclei via Hoechst stain (*$p<0.01$; compared to untransfected). This is compared to less than 5% in untransfected cultures. Therefore, the transfection procedure itself seemed to be damaging to the cultures. Despite this increase in background apoptosis, a significant increase in apoptosis was seen in Pablo transfected cells. As shown in FIG. 1, at 30 hours post transfection, one hundred percent of rat hippocampal neurons transfected with Pablo displayed abnormal nuclear morphology of cells undergoing apoptosis as evidenced by pyknotic nuclei (**$p<0.01$ compared to eGFP empty vector transfected).

Example 4

Pablo Overexpression is Toxic in PC12 Cells

Stable PC12 cell lines expressing Pablo were made using the PC12 Tet-Off cell line (commercially available from Clontech; Palo Alto, Calif.). Plasmids to be used in the generation of Tet-regulated stably expressing neuronal cell lines were constructed. The regulation of the expressed gene is brought about by the double stable expression first of a "regulator" plasmid, which contains the tet-controlled transactivator (tTA) and a second "response" plasmid, which contains a gene of interest, in this case Pablo, under the control of a promoter sequence that includes the tetracycline response element (TRE). The commercially avialable regulator plasmids are in vectors engineered for neomycin selection, necessitating that response vectors be constructed to include a second selectable marker. The starting material for the construction of the response plasmid was pcDNA3.1 (-). This vector is zeocin selectable, but contains a constitutively active CMV promoter. Therefore, the first step in construction was the removal of this promoter by digestion with MnuI (upstream of the promoter) and NheI (downstream of the promoter; also the most upstream site in the polylinker). Blunting of the resulting incompatible ends and ligation to recircularize the plasmid resulted in a promoterless vector. The second step was the insertion of the TRE. This element was removed as a 450 bp. fragment from by digestion with XhoI and EcoRI. The promoterless vector, similarly cut, received the TRE insert, resulting in a TRE-driven response vector suitable to house the Pablo gene under the control of the TRE. This vector has a somewhat limited polylinker, however, with only EcoRI, BamHI, and HindIII as usable sites. Pablo was cloned into the BamHI site. Pablo expression was turned off in the presence of tetracycline or a tetracycline-related compound (e.g., doxycycline) and turned on when tetracycline is not added to the culture medium. Construction of this vector permits the stable expression of Pablo in cells in which it is normally toxic.

For transfection, briefly, cells were cultured in DMEM with additives (10% horse serum, 5% fetal bovine serum, antibiotics (100 U/ml penicillin G sodium and 100 ug/ml streptomycin sulfate), and 2 mM L-glutamine). After approximately 48 hours the medium was changed to DMEM comprising additives and 100 ug/ml G418 (Gibco BRL). Cells were expanded and the G418 concentration was decreased to 50 ug/ml. Cells were transferred to medium comprising Doxycyclin and the cells were transfected with constructs comprising the full length Pablo gene (approximately 50 ug of DNA) using the Promega Profectin (CaPO$_4$) system according to the manufacturer's instructions. After approximately 16 hours, the cells were washed and resuspended in DMEM with additives and doxycyclin. After approximately, 48 hours the cells were placed in DMEM comprising zeocin.

Figure 2:
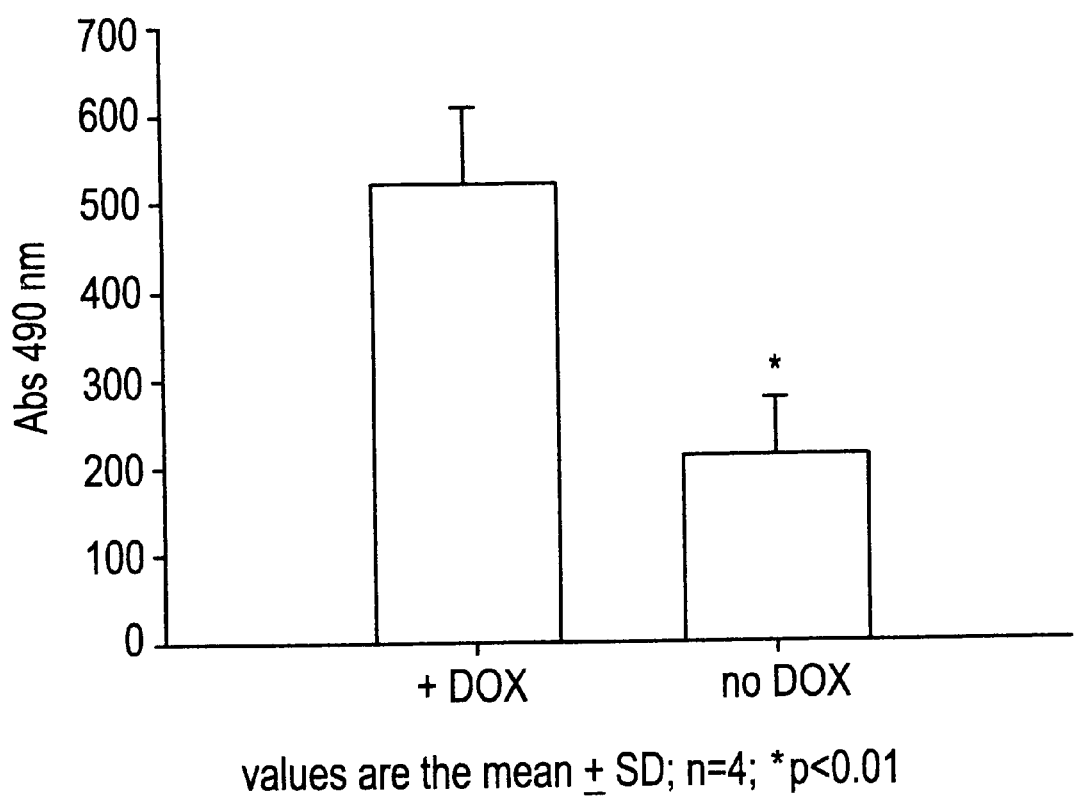
FIG. 2 shows that PC12 cells that do not express Pablo were viable, while PC12 cells in which Pablo expression was induced (no DOX) were less viable.

The stably transformed heterogeneous population of PC12-Pablo cells were induced or not induced for 48 hours Viable cells were detected by measuring MTS (Cell titer 96 Aqueous; Promega) reducing activity in these cultures. The assay is based on the cellular conversion of the tetrazolium salt, MTS [3-(4,5-dimethylthiazol-2-yl)-5-(3carboxymethoxyphenyl)-2-(4-sulphophenyl)-2H-tetrazolium, inner salt], into a formazan product that is soluble in tissue culture medium and is measured at 490 nm directly in 96 well assay plates without additional processing (1–3). Absorbance is directly proportional to the number of living cells in culture. The data are presented as optical density at 490 nm; cultures with greater optical density contain more viable cells. As shown in FIG. 2, after a 90 minute incubation at 37C, uninduced (+Dox) cultures had an OD490 nm of 0.517. By comparison, cultures in which Pablo expression was induced had an OD490 nm of 0.209.

Figure 3:
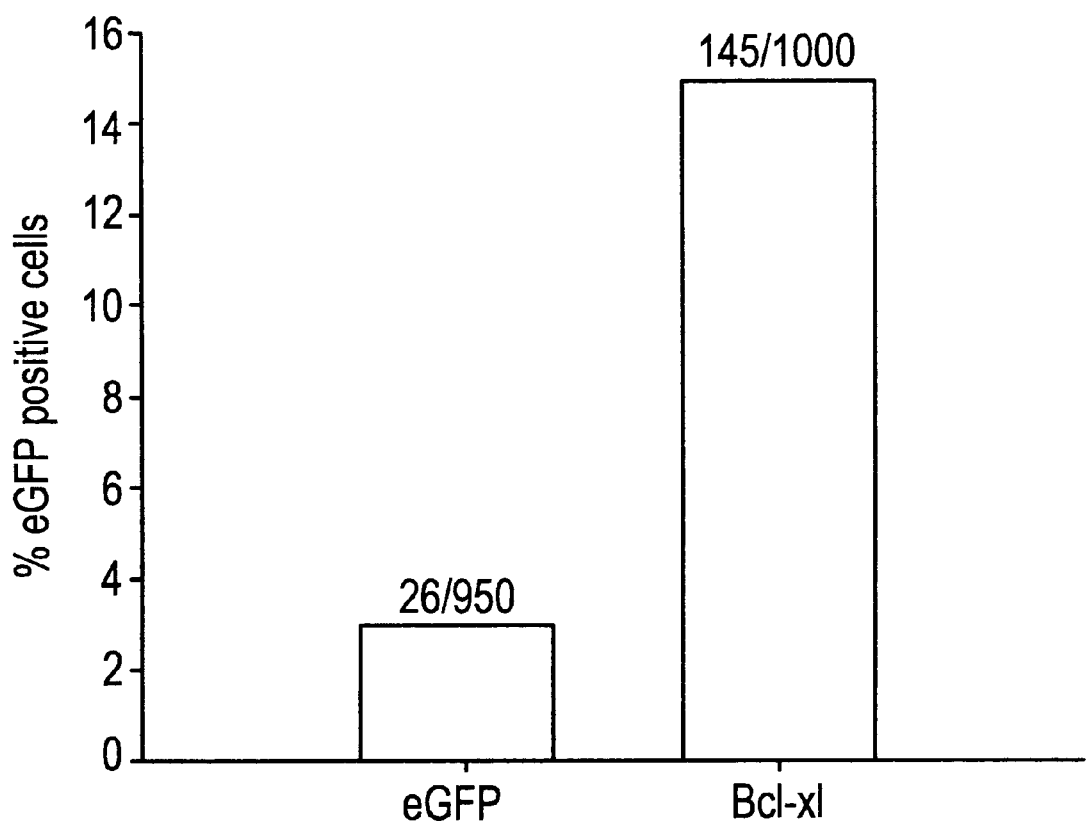
FIG. 3 shows the percentage of Pablo expressing PC12 cells that were positive for green fluorescent protein (GFP+) 48 hours post-transfection/induction. The data are shown for Pablo expressing cells transfected with the eGFP vector alone (eGFP) or Pablo expressing cells transfected with the eGFP vector+Bcl-xL (Bcl-xL).
Figure 4:
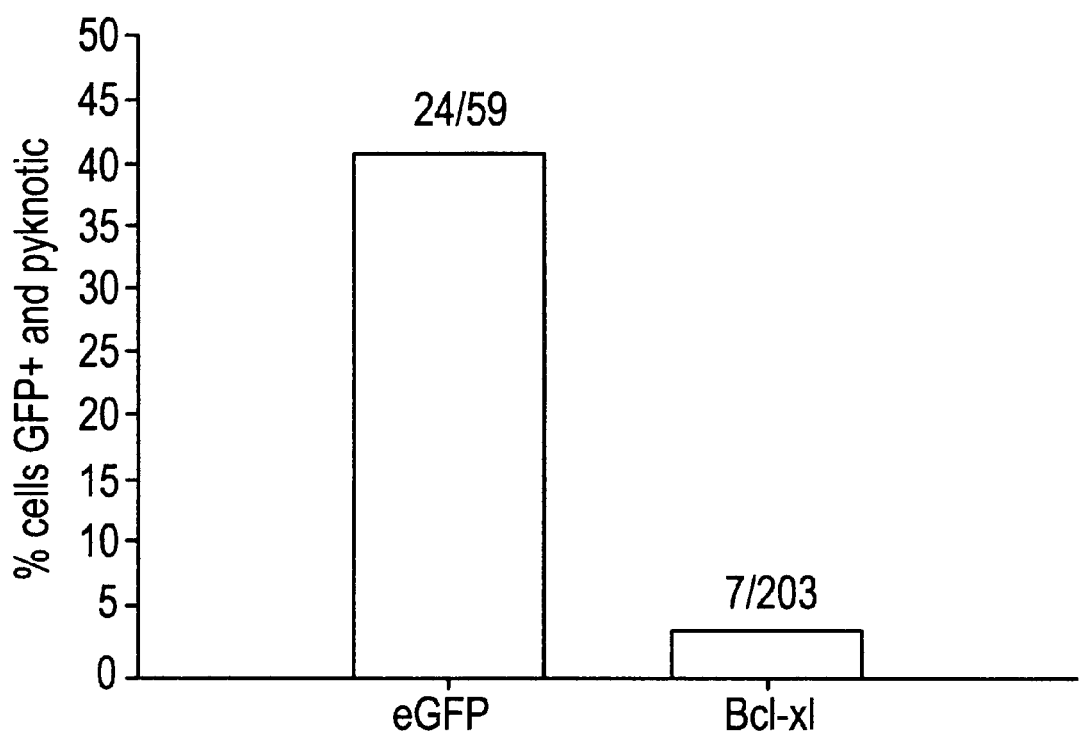
FIG. 4 shows that only 3.5% of Pablo expressing PC12 cells transfected with the eGFP vector containing Bcl-xL (Bcl-xL) showed apoptotic nuclei at 48 hours post-transfection/induction.

Hoechst staining data suggests that Pablo-induced cell death is an apoptotic death. Also, as shown in Example 1, Pablo was identified in a two hybrid screen because of its Bcl-xL binding activity. Therefore, Bcl-xL's ability to attenuate Pablo-induced cell death was examined. The stable, heterogeneous PC12-Pablo population was transiently transfected with either Bcl-xl-eGFP (green fluorescent protein) or eGFP empty vector. At the same time, Pablo expression was induced by the removal of doxycycline from the culture medium. FIG. 3 shows the percentage of PC12 cells that were eGFP+, 48 hours post-transfection/induction. Approximately 14% of the cells in the Bcl-xl transfected cultures were eGFP+. Only 2.7% of the cells in the eGFP empty vector transfected cultures were eGFP+. This apparent variability in transfection efficiencies is explained by the fact that approximately 40% of the eGFP transfected cells were undergoing apoptosis. In contrast, only 3.5% of cells transfected with Bcl-xL-eGFP showed apoptotic nuclei at 48 hours post-transfection/induction. (see FIG. 4). Therefore, the apparent lower transfection efficiency of the eGFP empty vector is likely due to the death of cells at a time before 48 hours Example 5

Pablo Over-expression is not Toxic to HEK 293 Cells

HEK 293 cells were transfected with the Pablo-eGFP-C2 construct using the calcium phosphate ProFectin® Mammalian Transfection System (Promega Corporation, Madison, Wis.). Confocal image of 293 cells were examined 48 hours post-transfection. At this point, cell and nuclear morphology were normal and there was no evidence of cell death. The Pablo distribution was diffuse cytoplasmic, and absent from the nucleus. At none of time points examined, (8, 24, 48 hours) was there any specific localization to the plasma membrane as seen in the CGNs at early times.

Figure 5:
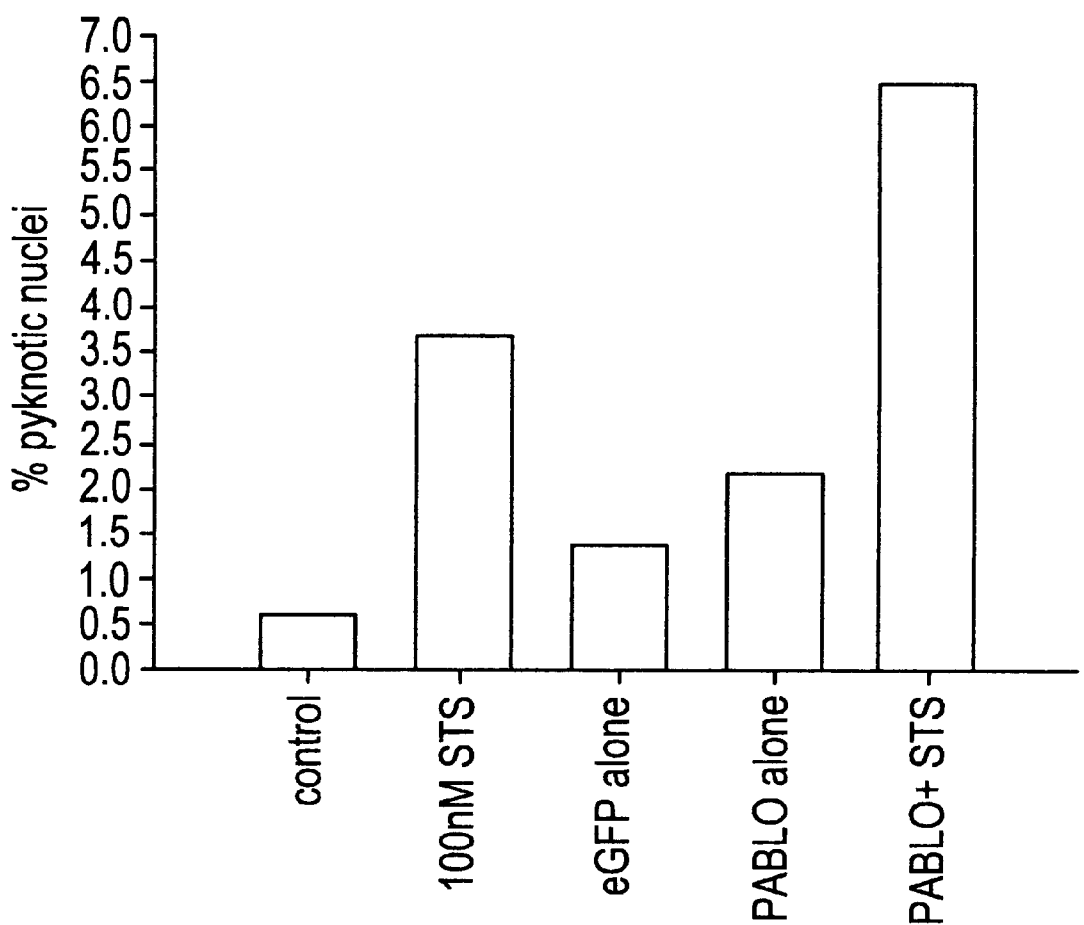
FIG. 5 shows that there was no statistically significant increase in pyknotic nuclei in 293 cells expressing Pablo (Pablo alone) as compared to cells expressing the eGFP vector alone.
Figure 6:
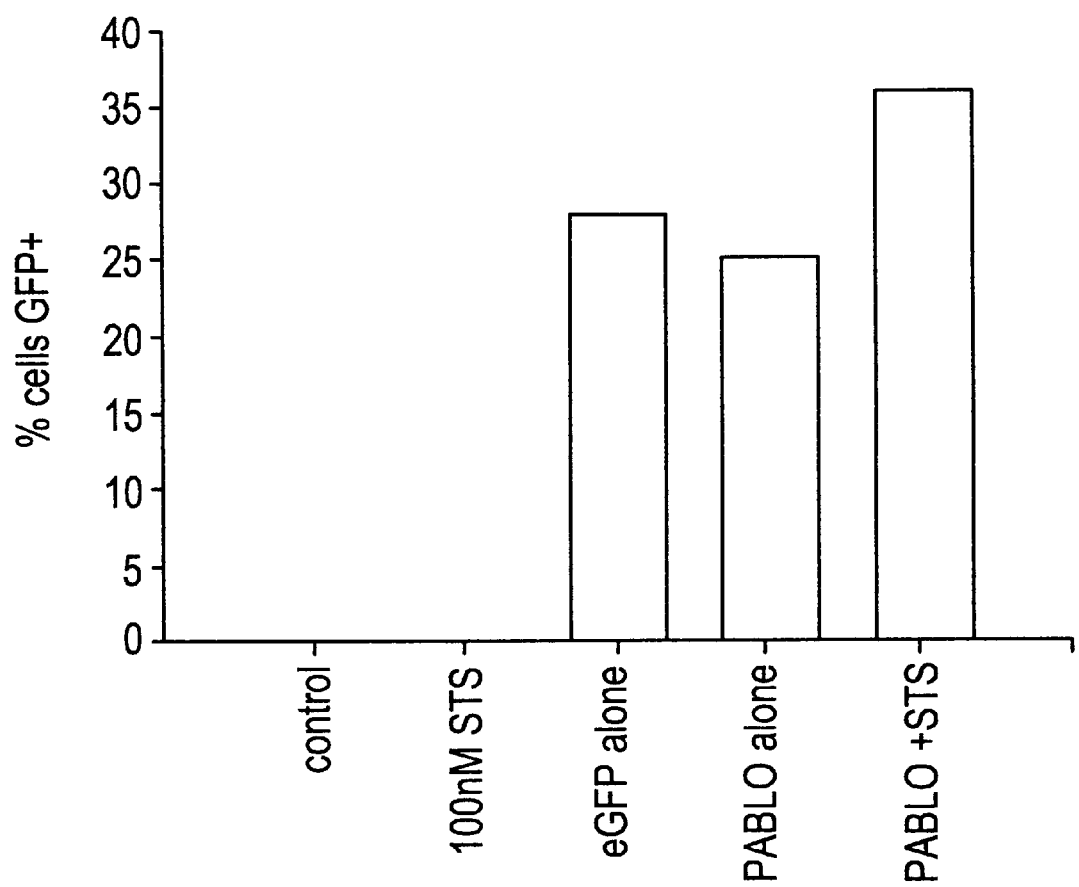
FIG. 6 shows that the 293 cells receiving vector alone or vector+Pablo in FIG. 5 were transfected at roughly the same efficiency.
Figure 7:
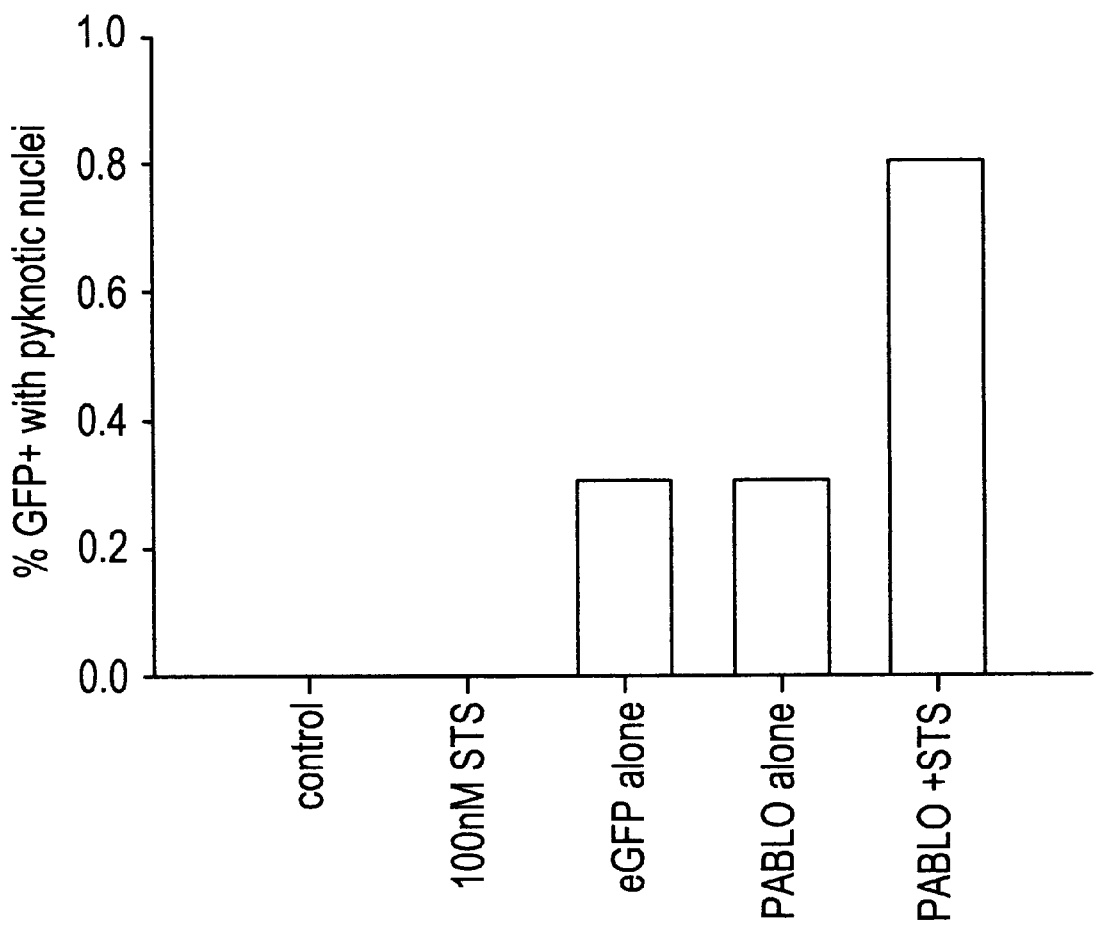
FIG. 7 shows that the 293 cells receiving vector alone or vector+Pablo in FIG. 5 had roughly the same percentage of cells with pyknotic nuclei when only GFP+ cells were measured.
Figure 8A:
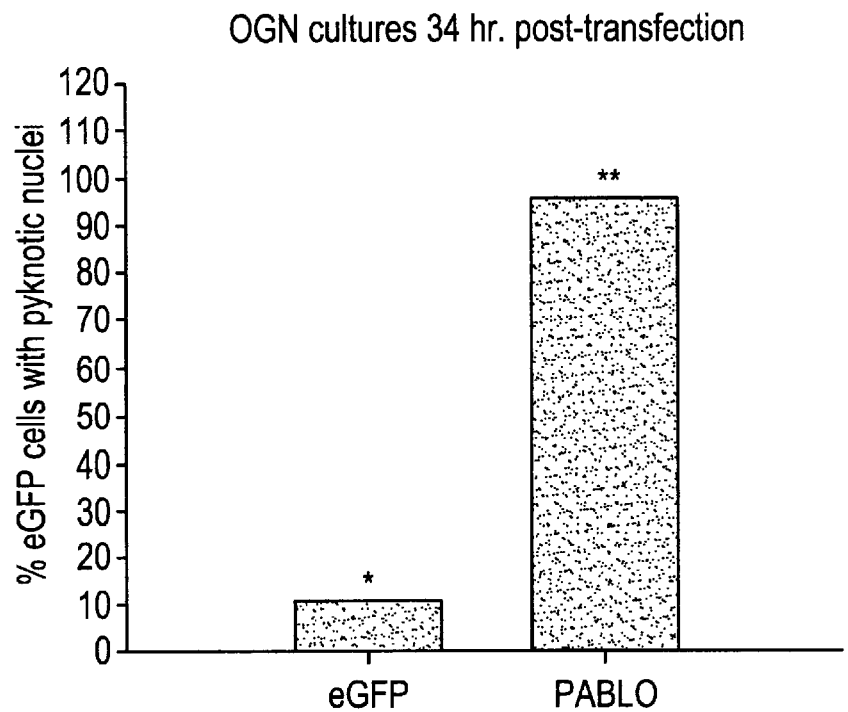
FIG. 8 shows that Pablo transfection causes apoptosis in neuronal cells and not in non-neuronal cells.
Figure 8B:
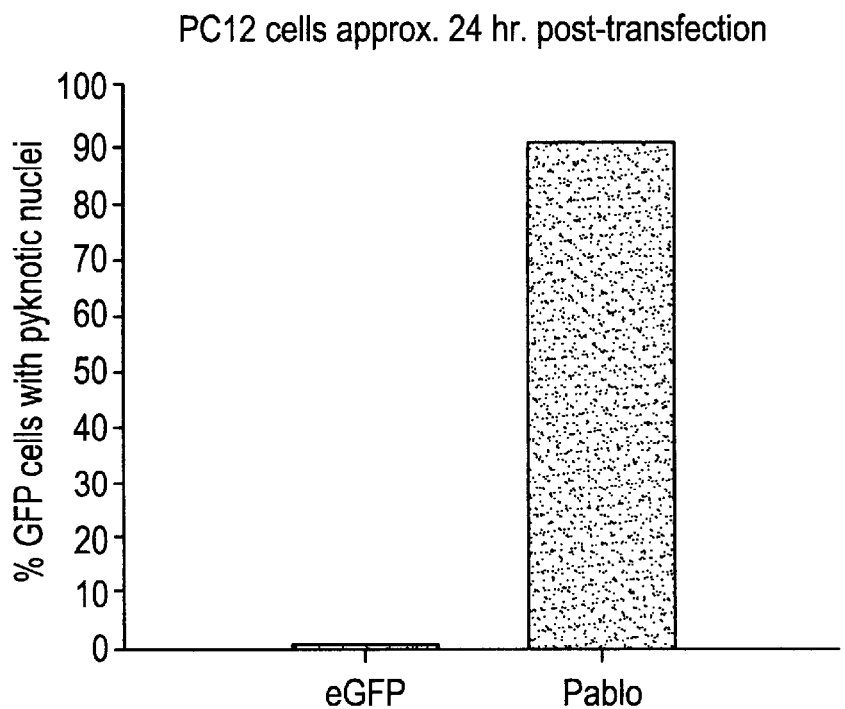
Figure 8C:
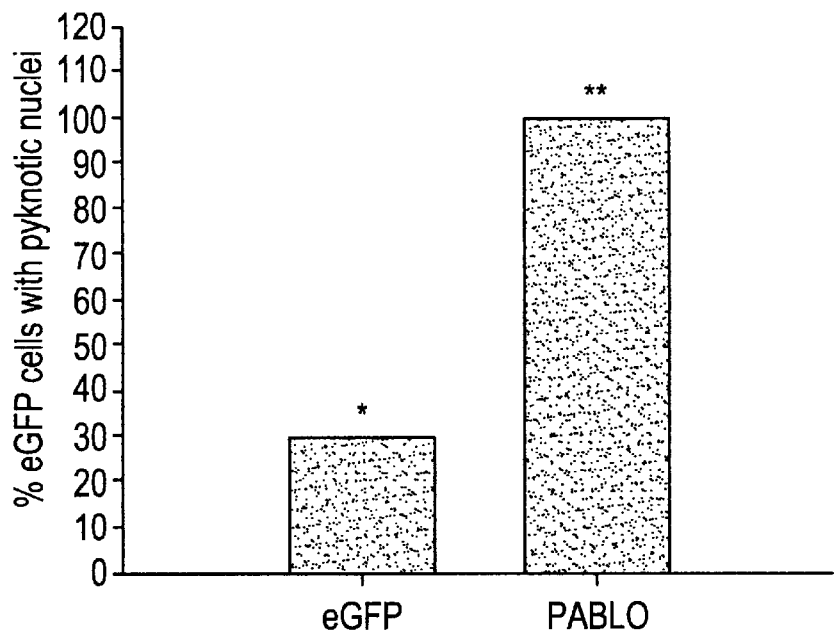
Figure 8D:
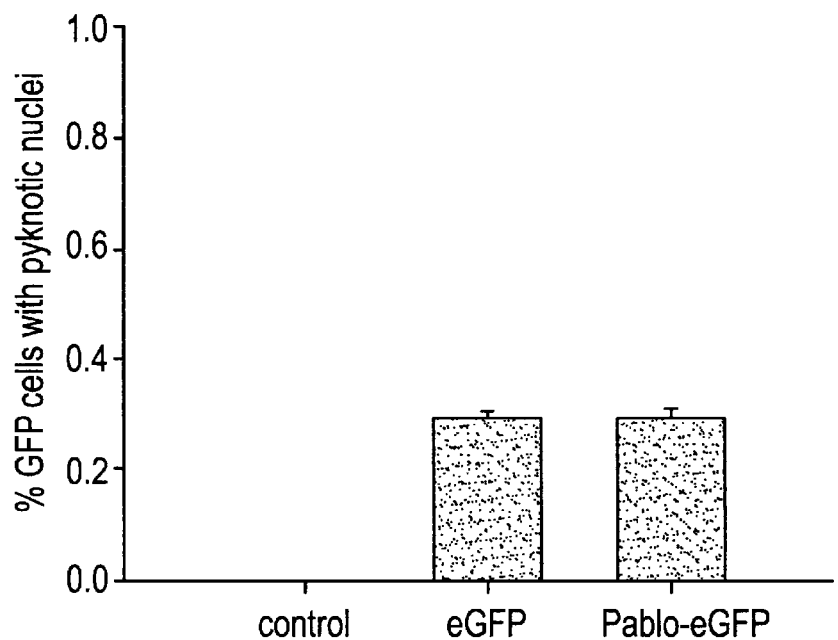

Table 1 summarizes data from 3 separate experiments in which HEK 293 cells in 6 well plates were transfected with Pablo-eGFP-C2. As controls, some cultures were transfected with the empty eGFP vector and others were left untransfected. In these experiments, the toxicity of Pablo overexpression was examined as well as effects of Pablo overexpression on vulnerability to a subsequent insult (in this case staurosporine (STS)). The percentage of cells having pyknotic nuclei is shown in FIG. 5 and the percentage of GFP+ cells is shown in FIG. 6. FIG. 5 shows the percentage of pyknotic nuclei as revealed by Hoechst staining of 293 cells 48 hours post-transfection. By CHI-Squared analysis, there was no statistically significant increase in pyknotic nuclei in the Pablo transfected cultures versus the eGFP cultures. Also, the fold increase in cell loss by staurosporine does not appear to be any more severe in the Pablo transfected cultures than when comparing the staurosporine effect in untransfected cultures. FIG. 6 shows that the transfection efficiencies were roughly equivalent for the three transfected groups. The percentage of GFP+ cells having pyknotic nuclei at 48 hours post transfection is shown in FIG. 7. FIG. 7 reports the data looking specifically at the nuclei of eGFP positive cells. Again, there is no difference between eGFP alone and the Pablo-eGFP fusion construct. Briefly, Pablo was neither toxic when expressed alone, nor did it enhance the toxicity of a staurosporine insult.

TABLE 1

HEK 293 cells

|  | pyknotic nuclei | GFP+ | GFP+ and Pyknotic | Percent pyknotic nuclei | Percent GFP+ | % GFP+ and pyknotic nucle |
|---|---|---|---|---|---|---|
| control | 7/1100 | n/a | N/a | 0.6 |  |  |
| eGFP | 10/690 | 193 | 1 | 1.4 | 28 | 0.5 |
| Pablo alone | 28/1262 | 318 | 1 | 2.2 | 25 | 0.3 |
| 100 nM STS | 19/516 | n/a | n/a | 3.7 |  |  |
| Pablo + STS | 69/1058 | 387 | 3 | 6.5 | 36 | 0.8 |

For table 1, Cells were observed 48 hours post-transfection with Pablo; treatment with STS was for 24 hours and was added 24 hours post-transfection.

The effects of Pablo transfection on neuronal and non-neuronal cells are summarized in FIG. 8. As shown in that Figure, in addition to being predominantly expressed in neuronal cells, Pablo appears to be neuronal cell specific in its activity.

Example 6

Identification of the Bcl-xL Binding Region of Pablo

SEQ ID NO:2 shows the amino acid sequence of the full length Pablo used in these experiments. Three of the clones isolated in the Bcl-xl yeast 2 hybrid screen contained portions of the Pablo cDNA. Two of the clones encoded approximately the last 130 amino acids. One of the clones encoded the last 213 amino acids. This suggests that the ability of Pablo to bind to Bcl-xl is contained within the C-terminal 130 amino acids, from about amino acids 429–559.

These results were confirmed by constructing a deletion mutant of Pablo (Δ142) lacking the C-terminal 140 amino acids, amino acids 419–559. To construct Pablo (Δ142) PCR reaction was run using the existing Pablo-eGFP fusion vector and the following two primers:

1) tagaattc atg ccg cta gtg aaa aga aac atc g (SEQ ID NO: 7)

2) taggatcc acc ttg tgg gag tgg atg aac tgg (SEQ ID NO: 8)

Primer 1 is the 5' forward primer that has an EcoRI site immediately 5' to the ATG start codon. Primer 2 is the 3' reverse primer that has a BamHI site immediately 3' of Pablo nucleotide #1254 (after the ATG start). These two primers will yield a fragment which codes for amino acids 1–418 of Pablo. This PCR fragment was cloned into pCR2.1-TOPO (Invitrogen; cat# K4500-01). An EcoRI-BamHI digest of this yielded the Pablo delta 142 gene which was cloned into the EcoRI and BamHI sites of pEGFP-C2 (with the N-terminus of Pablo connected to the C-terminus of GFP in reading frame number 2; Clontech, cat# 6083-1). Using appropriate primers, the entire Pablo Δ142 construct was sequenced and confirmed. The nucleotide sequence is shown in SEQ ID NO:5 and the amino acid sequence is shown in SEQ ID NO:6.

Figure 9:
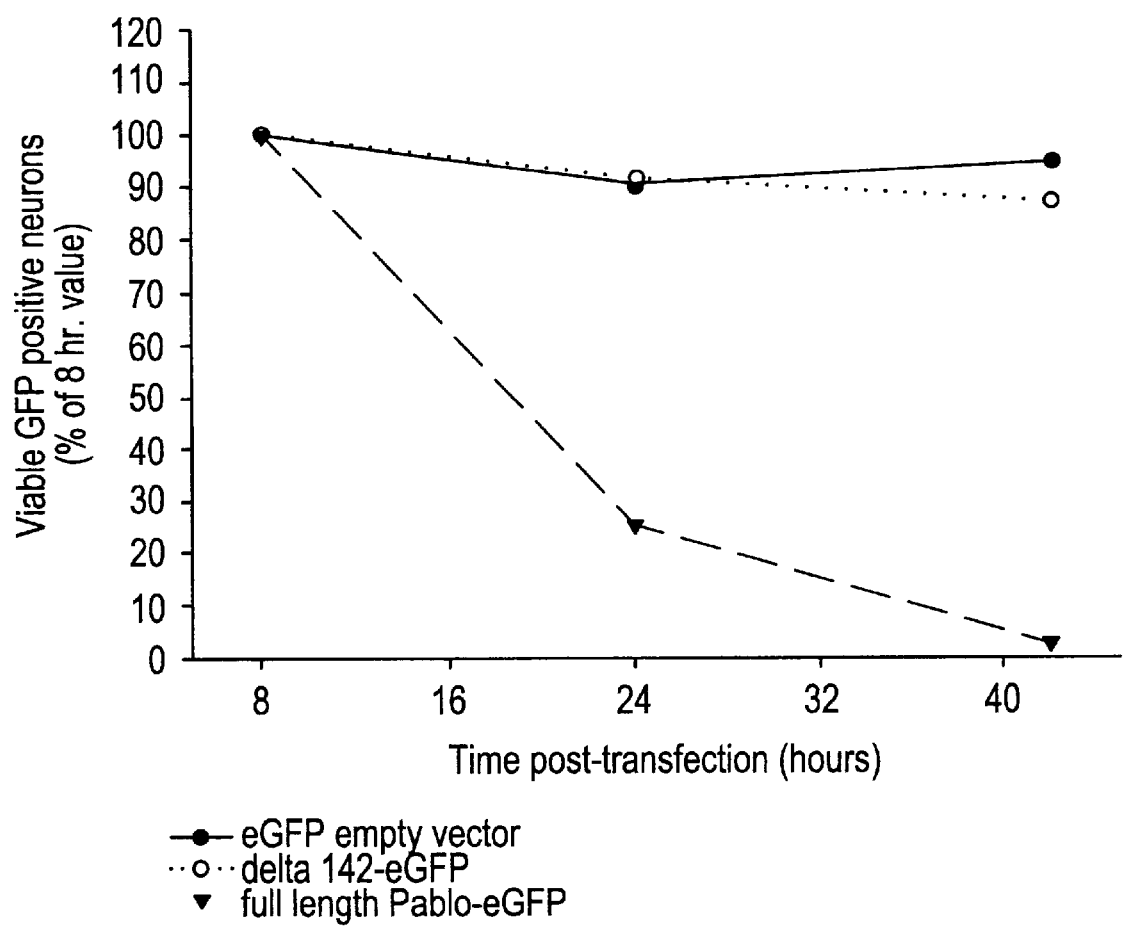
FIG. 9 shows the percentage of viable GFP positive neurons transfected with eGFP empty vector, the Pablo Δ142 mutant in the eGFP vector, or the full length Pablo-eGFP construct.

Rat cerebellar granular neurons were transiently transfected with full length Pablo; Pablo Δ142; and eGFP empty vector. At 8, 24, and 42 hours post transfection, cultures were fixed with 4% paraformaldehyde and Hoechst stained. Nuclei from GFP fluorescent cells were scored as apoptotic or normal. The results of this experiment are shown in FIG. 9. This Figure demonstrates that from about amino acids 419–559 of the Pablo protein are responsible for its apoptotic activity.

A second deletion mutant of Pablo was prepared lacking the 70 carboxy terminal amino acids of the protein, i.e., deleting amino acids 490–559. This construct is about 50% as effective as the full length Pablo protein in causing neural cell toxicity.

The region between the deletion sites in the Δ142 mutants (which show no neural cell toxicity) and the Δ70 mutants (which show about 50% of maximal toxicity), i.e., amino acids 436–489, is a region of great diversity between Pablo and WAVE2 and WAVE3 and, based on these results, may comprise the Bcl-xL binding domain of Pablo.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An antibody which binds a Pablo polypeptide comprising an amino acid sequence of SEQ ID NO:2, wherein the antibody inhibits a Pablo/Bcl-xL binding interaction.

2. The antibody of claim 1, wherein the antibody binding site is comprised within about amino acid 419 through amino acid 559 of SEQ ID NO:2.

3. An antibody which binds a Pablo polypeptide fragment comprising amino acid 419 through amino acid 559 of SEQ ID NO:2.

4. An antibody which binds a Pablo polypeptide fragment consisting of amino acid 419 through amino acid 559 of SEQ ID NO:2.

5. An antibody which binds a Pablo polypeptide fragment consisting of amino acid 429 through amino acid 559 of SEQ ID NO:2.

6. An antibody which binds a Pablo Bcl-xL polypeptide dimer.

7. An antibody as in one of claims 1–6, wherein the antibody inhibits apoptosis.

8. An antibody as in one of claims 1–6, wherein the antibody is a monoclonal antibody.

* * * * *

SEQUENCE LISTING

<160> NUMBER OF SEQ ID NOS: 2

<210> SEQ ID NO 1
<211> LENGTH: 2625
<212> TYPE: DNA
<213> ORGANISM: Homo sapiens

<400> SEQUENCE: 1

| | | | | | |
|---|---|---|---|---|---|
| cttctcttgc | acttgcggat | gatgaactgg | aataacgatg | aaagaaagca | catccgatct    60 |
| caacattcac | gtcctgccct | ataaccgatt | aattaattga | tccccagcta | gactagtgtt   120 |
| ggagaaatca | gcatgttaaa | acaactgttg | atgatagctg | ttggagtaaa | gttgcagtgg   180 |
| aagctatggc | tgcaaaatcg | ttaaaatctt | caaggtgaac | tggcacaaag | gttaatctca   240 |
| agatgccgct | agtgaaaaga | acatcgatc | ctaggcactt | gtgccacaca | gcactgccta   300 |
| gaggcattaa | gaatgaactg | gaatgtgtaa | ccaatatttc | cttggcaaat | ataattagac   360 |
| aactaagtag | cctaagtaaa | tatgctgaag | atatatttgg | agaattattc | aatgaagcac   420 |
| atagtttttc | cttcagagtc | aactcattgc | aagaacgtgt | ggaccgttta | tctgttagtg   480 |
| ttacacagct | tgatccaaag | gaagaagaat | tgtctttgca | agatataaca | atgaggaaag   540 |
| ctttccgaag | ttctacaatt | caagaccagc | agcttttcga | tcgcaagact | ttgcctattc   600 |
| cattacagga | gacgtacgat | gtttgtgaac | agcctccacc | tctcaatata | ctcactcctt   660 |
| atagagatga | tggtaaagaa | ggtctgaagt | tttataccaa | tccttcgtat | ttctttgatc   720 |
| tatggaaaga | aaaaatgttg | caagatacag | aggataagag | gaaggaaaag | aggaagcaga   780 |
| agcagaaaaa | tctagatcgt | cctcatgaac | cagaaaaagt | gccaagagca | cctcatgaca   840 |
| ggcggcgaga | atggcagaag | ctggcccaag | gtccagagct | ggctgaagat | gatgctaatc   900 |
| tcttacataa | gcatattgaa | gttgctaatg | cccagcctc  | tcattttgaa | acaagacctc   960 |
| agacatacgt | ggatcatatg | gatggatctt | actcactttc | tgccttgcca | tttagtcaga  1020 |
| tgagtgagct | tctgactaga | gctgaggaaa | gggtattagt | cagaccacat | gaaccacctc  1080 |
| cacctccacc | aatgcatgga | gcaggagatg | caaaaccgat | acccacctgt | atcagttctg  1140 |
| ctacaggttt | gatagaaaat | cgccctcagt | caccagctac | aggcagaaca | cctgtgtttg  1200 |
| tgagccccac | tcccccacct | cctccaccac | ctcttccatc | tgccttgtca | acttcctcat  1260 |
| taagagcttc | aatgacttca | actcctcccc | ctccagtacc | tccccacct  | ccacctccag  1320 |
| ccactgcttt | gcaagctcca | gcagtaccac | cacctccagc | tcctcttcag | attgcccctg  1380 |
| gagttcttca | cccagctcct | cctccaattg | cacctcctct | agtacagccc | tctccaccag  1440 |
| tagctagagc | tgccccagta | tgtgagactg | taccagttca | tccactccca | caaggtgaag  1500 |
| ttcagggggct | gcctccaccc | ccaccaccgc | tccctctgcc | tccacctggc | attgaccat  1560 |
| catcacctgt | cacagttaca | gctcttgctc | atcctccctc | tgggctacat | ccaactccat  1620 |
| ctactgcccc | aggtccccat | gttccattaa | tgcctccatc | tcctccatca | caagttatac  1680 |
| ctgcttctga | gccaaagcgc | catccatcaa | ccctacctgt | aatcagtgat | gccaggagtg  1740 |
| tgctactgga | agcaatacga | aaaggtattc | agctacgcaa | agtagaagag | cagcgtgaac  1800 |
| aggaagctaa | gcatgaacgc | attgaaaacg | atgttgccac | catcctgtct | cgccgtattg  1860 |
| ctgttgaata | tagtgattcg | gaagatgatt | cagaatttga | tgaagtagat | tggttggagt  1920 |
| aagaaaaatg | cattgataaa | tattacaaaa | ctgaatgcaa | atgtcctttg | tggtgcttgt  1980 |
| tccttgaaaa | tgtttggtca | ttctagtgtt | ttgctttctt | ttccttataa | taaatgaccc  2040 |

-continued

```
ttttcctcca taactttga tttctaagga aaatattagc atacatttca aactaaatgt    2100
tttacagtgg cttatctttt ttttccccct gaaaagacta atttggtcaa ataaaccact    2160
aagtattaag catggacagc tgttgttaga gtagcagatt cagttttttg atatatctta    2220
attgtgtact ttgtgaattt taatttaaag aaagcaactg aaattgaaat cttgagggca    2280
gctgtatcta ctaatgagcc ttattccatt tcctgatgtt ttaaaagaag aaacactgcc    2340
ttgattatac gaatacactc agaaagtaca tttagcttgt agtgttgaat tctcttaaag    2400
gaatgcttga attttttcat tattgtttta ttgtttttat atacttgcct tatttgaatg    2460
tttagcagta tccccttccc acttatatat tgtgtgatat gattttgctt gcctatagga    2520
gttaaaaact tttccatgtg aaatactctg acttaaacat acatgtaact tacataactg    2580
ttaagaataa cagtctgatt taataaatgg ttcattttaa aagtt              2625
```

<210> SEQ ID NO 2
<211> LENGTH: 559
<212> TYPE: PRT
<213> ORGANISM: Homo sapiens

<400> SEQUENCE: 2

```
Met Pro Leu Val Lys Arg Asn Ile Asp Pro Arg His Leu Cys His Thr
 1               5                  10                  15

Ala Leu Pro Arg Gly Ile Lys Asn Glu Leu Glu Cys Val Thr Asn Ile
                20                  25                  30

Ser Leu Ala Asn Ile Ile Arg Gln Leu Ser Ser Leu Ser Lys Tyr Ala
            35                  40                  45

Glu Asp Ile Phe Gly Glu Leu Phe Asn Glu Ala His Ser Phe Ser Phe
        50                  55                  60

Arg Val Asn Ser Leu Gln Glu Arg Val Asp Arg Leu Ser Val Ser Val
     65                  70                  75                  80

Thr Gln Leu Asp Pro Lys Glu Glu Leu Ser Leu Gln Asp Ile Thr
                85                  90                  95

Met Arg Lys Ala Phe Arg Ser Ser Thr Ile Gln Asp Gln Gln Leu Phe
            100                 105                 110

Asp Arg Lys Thr Leu Pro Ile Pro Leu Gln Glu Thr Tyr Asp Val Cys
        115                 120                 125

Glu Gln Pro Pro Leu Asn Ile Leu Thr Pro Tyr Arg Asp Asp Gly
    130                 135                 140

Lys Glu Gly Leu Lys Phe Tyr Thr Asn Pro Ser Tyr Phe Phe Asp Leu
145                 150                 155                 160

Trp Lys Glu Lys Met Leu Gln Asp Thr Glu Asp Lys Arg Lys Glu Lys
                165                 170                 175

Arg Lys Gln Lys Gln Lys Asn Leu Asp Arg Pro His Glu Pro Glu Lys
            180                 185                 190

Val Pro Arg Ala Pro His Asp Arg Arg Glu Trp Gln Lys Leu Ala
        195                 200                 205

Gln Gly Pro Glu Leu Ala Glu Asp Asp Ala Asn Leu His Lys His
    210                 215                 220

Ile Glu Val Ala Asn Gly Pro Ala Ser His Phe Glu Thr Arg Pro Gln
225                 230                 235                 240

Thr Tyr Val Asp His Met Asp Gly Ser Tyr Ser Leu Ser Ala Leu Pro
                245                 250                 255

Phe Ser Gln Met Ser Glu Leu Leu Thr Arg Ala Glu Glu Arg Val Leu
            260                 265                 270
```

-continued

```
Val Arg Pro His Glu Pro Pro Pro Pro Pro Met His Gly Ala Gly
        275                 280                 285

Asp Ala Lys Pro Ile Pro Thr Cys Ile Ser Ser Ala Thr Gly Leu Ile
        290                 295                 300

Glu Asn Arg Pro Gln Ser Pro Ala Thr Gly Arg Thr Pro Val Phe Val
305                 310                 315                 320

Ser Pro Thr Pro Pro Pro Pro Pro Pro Leu Pro Ser Ala Leu Ser
                325                 330                 335

Thr Ser Ser Leu Arg Ala Ser Met Thr Ser Thr Pro Pro Pro Val
            340                 345                 350

Pro Pro Pro Pro Pro Pro Ala Thr Ala Leu Gln Ala Pro Ala Val
        355                 360                 365

Pro Pro Pro Pro Ala Pro Leu Gln Ile Ala Pro Gly Val Leu His Pro
    370                 375                 380

Ala Pro Pro Pro Ile Ala Pro Pro Leu Val Gln Pro Ser Pro Pro Val
385                 390                 395                 400

Ala Arg Ala Ala Pro Val Cys Glu Thr Val Pro Val His Pro Leu Pro
                405                 410                 415

Gln Gly Glu Val Gln Gly Leu Pro Pro Pro Pro Pro Pro Pro Leu
            420                 425                 430

Pro Pro Pro Gly Ile Arg Pro Ser Ser Pro Val Thr Val Thr Ala Leu
        435                 440                 445

Ala His Pro Pro Ser Gly Leu His Pro Thr Pro Ser Thr Ala Pro Gly
    450                 455                 460

Pro His Val Pro Leu Met Pro Pro Ser Pro Pro Ser Gln Val Ile Pro
465                 470                 475                 480

Ala Ser Glu Pro Lys Arg His Pro Ser Thr Leu Pro Val Ile Ser Asp
                485                 490                 495

Ala Arg Ser Val Leu Leu Glu Ala Ile Arg Lys Gly Ile Gln Leu Arg
            500                 505                 510

Lys Val Glu Glu Gln Arg Glu Gln Glu Ala Lys His Glu Arg Ile Glu
        515                 520                 525

Asn Asp Val Ala Thr Ile Leu Ser Arg Arg Ile Ala Val Glu Tyr Ser
    530                 535                 540

Asp Ser Glu Asp Asp Ser Glu Phe Asp Glu Val Asp Trp Leu Glu
545                 550                 555
```